(12) United States Patent
Folan

(10) Patent No.: US 11,419,741 B2
(45) Date of Patent: Aug. 23, 2022

(54) COVERED ENDOPROSTHESIS WITH IMPROVED BRANCH ACCESS

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/902,505

(22) Filed: Jun. 16, 2020

(65) Prior Publication Data

US 2020/0390573 A1    Dec. 17, 2020

Related U.S. Application Data

(60) Provisional application No. 62/862,599, filed on Jun. 17, 2019.

(51) Int. Cl.
| | |
|---|---|
| *A61F 2/90* | (2013.01) |
| *A61F 2/848* | (2013.01) |
| *A61F 2/856* | (2013.01) |
| *A61F 2/04* | (2013.01) |

(52) U.S. Cl.
CPC ............. *A61F 2/90* (2013.01); *A61F 2/848* (2013.01); *A61F 2/856* (2013.01); *A61F 2/04* (2013.01); *A61F 2002/8486* (2013.01); *A61F 2210/0076* (2013.01); *A61F 2220/0016* (2013.01)

(58) Field of Classification Search
None
See application file for complete search history.

(56) References Cited

U.S. PATENT DOCUMENTS

| | | | |
|---|---|---|---|
| 5,575,818 | A | 11/1996 | Pinchuk |
| 5,741,333 | A | 4/1998 | Frid |
| 6,264,689 | B1 | 7/2001 | Colgan et al. |
| 6,468,303 | B1 | 10/2002 | Amplatz et al. |

(Continued)

FOREIGN PATENT DOCUMENTS

| | | |
|---|---|---|
| EP | 0808138 B1 | 10/2005 |
| EP | 0957773 B1 | 6/2011 |

(Continued)

OTHER PUBLICATIONS

International Search Report and Written Opinion dated Sep. 14, 2020 for International Application No. PCT/US2020/037873.

*Primary Examiner* — Leslie Lopez
(74) *Attorney, Agent, or Firm* — Seager, Tufte & Wickhem, LLP

(57) ABSTRACT

An endoprosthesis may include an expandable framework including an anchoring portion and a body portion extending axially from the anchoring portion, the body portion having a plurality of body cells; and a polymeric cover disposed on at least a portion of the expandable framework. The anchoring portion includes a first transverse flange and a second transverse flange proximate the first transverse flange, the first and second transverse flanges being configured to secure the anchoring portion at an orifice of a body lumen. The body portion includes a window through a side of the body portion, the window occupying space equivalent to at least two of the plurality of body cells. The window is devoid of the polymeric cover and any other structure within a perimeter of the window.

13 Claims, 18 Drawing Sheets

(56) References Cited

U.S. PATENT DOCUMENTS

| | | |
|---|---|---|
| 6,616,675 B1 | 9/2003 | Evard et al. |
| 6,620,122 B2 | 9/2003 | Stinson et al. |
| 6,663,663 B2 | 12/2003 | Kim et al. |
| 7,018,401 B1* | 3/2006 | Hyodoh ............... D04C 3/48 623/1.12 |
| 7,115,136 B2 | 10/2006 | Park et al. |
| 7,311,031 B2 | 12/2007 | McCullagh et al. |
| 7,462,192 B2 | 12/2008 | Norton et al. |
| 7,591,845 B2 | 9/2009 | Rhim et al. |
| 7,670,367 B1 | 3/2010 | Chouinard et al. |
| 7,763,011 B2 | 7/2010 | Ortiz et al. |
| 8,114,147 B2 | 2/2012 | Wood et al. |
| 8,151,682 B2 | 4/2012 | Lilburn et al. |
| 8,357,193 B2 | 1/2013 | Phan et al. |
| 8,454,632 B2 | 6/2013 | Binmoeller et al. |
| 8,677,874 B2 | 3/2014 | Lilburn et al. |
| 9,265,634 B2 | 2/2016 | Brady et al. |
| 9,301,862 B2 | 4/2016 | Jordan et al. |
| 9,539,126 B2 | 1/2017 | Walsh et al. |
| 9,675,473 B2 | 6/2017 | Clerc et al. |
| 10,076,330 B2 | 9/2018 | Sander et al. |
| 10,085,861 B2 | 10/2018 | Walsh et al. |
| 10,130,498 B2 | 11/2018 | Fleury et al. |
| 2003/0135265 A1 | 7/2003 | Stinson |
| 2004/0098099 A1 | 5/2004 | McCullagh et al. |
| 2006/0292206 A1* | 12/2006 | Kim ............... A61B 17/12195 424/443 |
| 2007/0123922 A1 | 5/2007 | Cooper et al. |
| 2007/0282453 A1 | 12/2007 | Weitzner et al. |
| 2008/0228256 A1* | 9/2008 | Erickson ............... A61F 2/064 623/1.11 |
| 2009/0082803 A1 | 3/2009 | Adams et al. |
| 2010/0049307 A1* | 2/2010 | Ren ............... A61F 2/07 623/1.35 |
| 2010/0191167 A1* | 7/2010 | Laufer ............... A61F 2/2476 604/8 |
| 2012/0150273 A1* | 6/2012 | Centola ............... A61F 2/07 623/1.35 |
| 2013/0012969 A1 | 1/2013 | Shin |
| 2014/0081416 A1 | 3/2014 | Clerc et al. |
| 2016/0081832 A1 | 3/2016 | Hingston et al. |
| 2016/0113789 A1 | 4/2016 | Fleury et al. |
| 2017/0086959 A1 | 3/2017 | Verin et al. |
| 2018/0280166 A1 | 10/2018 | Walsh et al. |
| 2018/0280669 A1 | 10/2018 | Shlomovitz et al. |
| 2018/0338846 A1* | 11/2018 | Folan ............... A61M 27/002 |

FOREIGN PATENT DOCUMENTS

| | | |
|---|---|---|
| EP | 2543323 A1 | 1/2013 |
| EP | 1558149 B1 | 12/2013 |
| EP | 2754415 B1 | 5/2015 |
| EP | 2177181 B1 | 6/2015 |
| WO | 9601599 A1 | 1/1996 |
| WO | 2009140195 A1 | 11/2009 |
| WO | 2015195893 A1 | 12/2015 |

* cited by examiner

COVERED ENDOPROSTHESIS WITH IMPROVED BRANCH ACCESS

CROSS-REFERENCE TO RELATED APPLICATIONS

This application claims the benefit of priority under 35 U.S.C. § 119 of U.S. Provisional Application No. 62/862,599 filed Jun. 17, 2019, the entire disclosure of which is hereby incorporated by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

One currently known and/or recommended treatment for relief of biliary blockage in the biliary tree is the placement of a covered endoprosthesis or stent within the restricted body lumen (e.g., the bile duct, the pancreatic duct, etc.), such as that caused by a stricture formation. For example, it may be necessary to open the body lumen (e.g., the bile duct, the pancreatic duct, etc.) to permit passing of bile and stone-related debris to relieve acute painful symptoms. Uncovered metallic endoprostheses or stents are sometimes placed for chronic conditions but are generally not removable. Plastic endoprostheses or stents may be prone to blockage which may require repeat treatment(s) and are sometimes unable to open the stricture that initially caused the blockage of the affected body lumen (e.g., the bile duct, the pancreatic duct, etc.). Additionally, the biliary tree has several branches, bifurcations, and/or adjoining lumens. Placement of a covered endoprosthesis or stent across a bifurcation and/or an opening of an adjacent branch or lumen to treat a stricture or blocked body lumen may result in additional blockage of a currently open or unrestricted lumen, which may be undesirable. There is an ongoing need to provide alternative endoprostheses or stents as well as alternative methods for manufacturing and using endoprostheses or stents.

SUMMARY

In a first aspect, an endoprosthesis may comprise an expandable framework including an anchoring portion and a body portion extending axially from the anchoring portion, the body portion having a plurality of body cells; and a polymeric cover disposed on at least a portion of the expandable framework. The anchoring portion may include a first transverse flange and a second transverse flange proximate the first transverse flange, the first and second transverse flanges being configured to secure the anchoring portion at an orifice of a body lumen. The body portion may include a window through a side of the body portion, the window occupying space equivalent to at least two of the plurality of body cells. The window may be devoid of the polymeric cover and any other structure within a perimeter of the window.

In addition or alternatively, the first transverse flange and the second transverse flange are axially spaced apart.

In addition or alternatively, the body portion is braided or woven.

In addition or alternatively, the body portion includes one or more filaments interwoven around a central longitudinal axis of the expandable framework.

In addition or alternatively, the window is formed by removing at least a portion of the one or more filaments.

In addition or alternatively, the perimeter of the window is at least partially defined by a plurality of welds joining the one or more filaments together.

In addition or alternatively, the window is positioned adjacent the anchoring portion.

In addition or alternatively, the body portion is configured to dilate the body lumen.

In addition or alternatively, a first body portion opposite the window relative to a central longitudinal axis of the expandable framework is configured to exert less radially outward force on the body lumen than a second body portion opposite the anchoring portion relative to the window.

In addition or alternatively, an endoprosthesis for maintaining patency of a body lumen may comprise an expandable framework including an anchoring portion, a body portion having a plurality of body cells, and a linking portion extending axially from the anchoring portion to the body portion; and a polymeric cover disposed on at least a portion of the expandable framework. The anchoring portion may include a first transverse flange and a second transverse flange proximate the first transverse flange, the first and second transverse flanges being configured to secure the anchoring portion at an orifice of a body lumen. The linking portion may include a plurality of longitudinally-oriented struts spacing the body portion from the anchoring portion, the linking portion being devoid of the polymeric cover.

In addition or alternatively, the body portion is coaxial with the anchoring portion.

In addition or alternatively, the plurality of longitudinally-oriented struts is parallel to a central longitudinal axis of the expandable framework.

In addition or alternatively, the plurality of longitudinally-oriented struts is axially longer than the anchoring portion.

In addition or alternatively, the body portion includes a flared end opposite the anchoring portion.

In addition or alternatively, the expandable framework further includes a tapered flange extending axially away from the anchoring portion and radially outward from the linking portion.

In addition or alternatively, an endoprosthesis for maintaining patency of a vessel lumen may comprise an expandable framework including a first braided portion, a second braided portion, and a linking portion extending axially from the first braided portion to the second braided portion; and a polymeric cover disposed on at least a portion of the expandable framework. The linking portion may include a plurality of longitudinally-extending struts spacing the first braided portion from the second braided portion, the linking portion being devoid of the polymeric cover.

In addition or alternatively, when deployed, the linking portion exerts less radially outward force upon the vessel lumen than the first braided portion and the second braided portion.

In addition or alternatively, the plurality of longitudinally-extending struts is angled inward toward a central longitudinal axis of the expandable framework between the first braided portion and the second braided portion.

In addition or alternatively, each of the plurality of longitudinally-extending struts includes a coiled portion extending between the first braided portion and the second braided portion.

In addition or alternatively, an axial length of the linking portion is variable.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
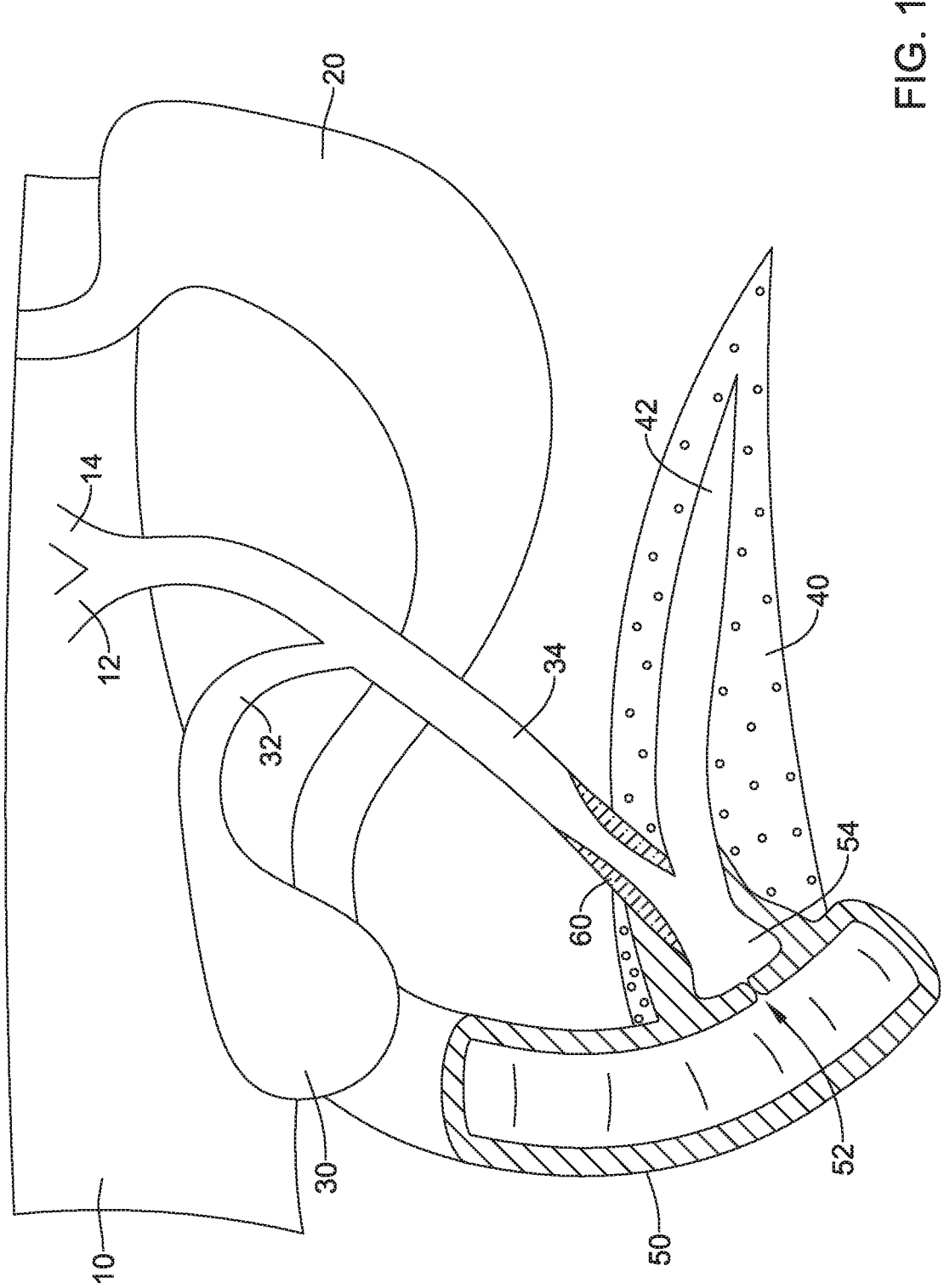
FIG. 1 illustrates aspects of a patient's biliary tree.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

FIG. 1 illustrates selected features and relative positioning of a patient's anatomy related to the biliary tree, including the liver 10, the left hepatic duct 12, the right hepatic duct 14, the stomach 20, the gallbladder 30, the cystic duct 32, the common bile duct 34, the pancreas 40, the pancreatic duct 42, the duodenum 50 (shown partially cut away), the papilla of Vater 52, and the ampulla of Vater 54. In some patients, a stricture 60 may form or develop that may partially or completely block a body lumen such as the common bile duct 34, the pancreatic duct 42, etc.

Figure 2:
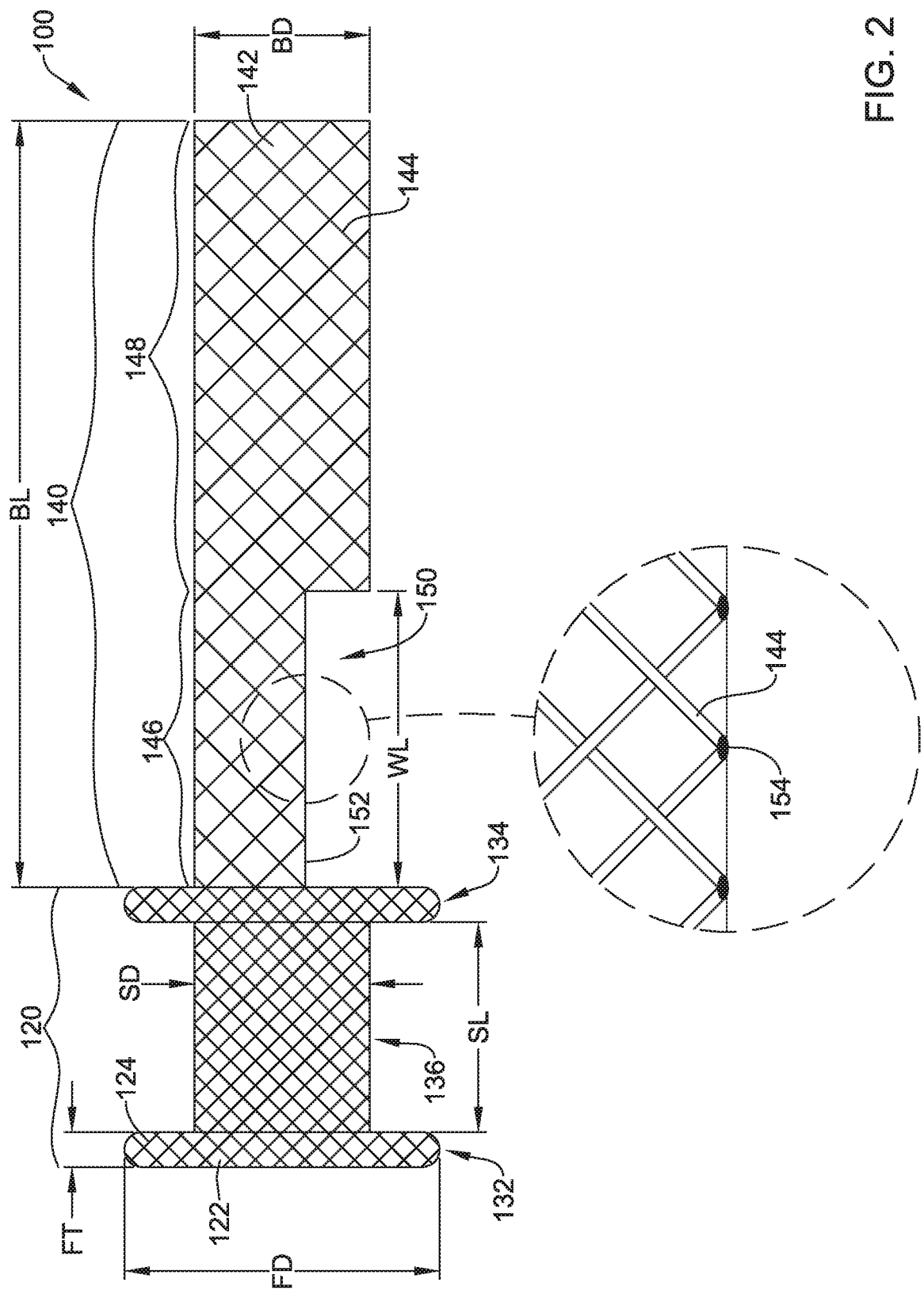
FIG. 2 illustrates aspects of an example endoprosthesis.

FIG. 2 illustrates an example endoprosthesis 100 (which term may be used interchangeably with the term "stent" herein) comprising an expandable framework including an anchoring portion 120 and a body portion 140 extending axially from the anchoring portion 120 along a central longitudinal axis of the endoprosthesis 100 and/or the expandable framework. The endoprosthesis 100 and/or the expandable framework may be configured to shift between a delivery configuration and a deployed configuration. The delivery configuration may be axially elongated and/or radially collapsed or compressed compared to the deployed configuration. The deployed configuration may be axially shortened and/or radially expanded compared to the delivery configuration. In at least some embodiments, the endoprosthesis 100 and/or the expandable framework may be self-expandable. For example, the endoprosthesis 100 and/or the expandable framework may be formed from a shape memory material. In some embodiments, the endoprosthesis 100 and/or the expandable framework may be mechanically expandable. For example, the endoprosthesis 100 and/or the expandable framework may be expandable using an inflatable balloon, using an actuation member, or other suitable means. During delivery to a treatment site, the endoprosthesis 100 and/or the expandable framework may be disposed within a lumen of a delivery sheath in the delivery configuration. Upon removal from the lumen of the delivery sheath, the endoprosthesis 100 and/or the expandable framework may be shifted to the deployed configuration.

As seen in the deployed configuration illustrated in FIG. 2, the anchoring portion 120 may have a plurality of anchoring cells 122. The anchoring portion 120 may include one or more filaments 124 interwoven around the central longitudinal axis of the endoprosthesis 100 and/or the expandable framework. The one or more filaments 124 of the anchoring portion 120 may form and/or define the plurality of anchoring cells 122. In the deployed configuration, the anchoring portion 120 may include a first transverse flange 132 and a second transverse flange 134 proximate the first transverse flange 132. The anchoring portion 120 may be substantially tubular and/or may include a lumen extending axially through the anchoring portion 120. The first transverse flange 132 and the second transverse flange 134 may be axially spaced apart by a saddle portion 136. In some embodiments, the saddle portion 136 may substantially define the lumen extending axially through the anchoring portion 120.

In some embodiments, the first transverse flange 132 and/or the second transverse flange 134 may each have an axial thickness FT or axial extent of about 0.5 millimeters to about 3 millimeters, about 1 millimeter to about 2 millimeters, or another suitable range. In some embodiments, the first transverse flange 132 and/or the second transverse flange 134 may each have a radial outer dimension FD or radial extent of about 15 millimeters to about 30 millimeters, about 17 millimeters to about 24 millimeters, about 18 millimeters to about 20 millimeters, or another suitable range. In some embodiments, the saddle portion 136 may have an axial length SL of about 2 millimeters to about 18 millimeters, about 5 millimeters to about 15 millimeters, about 8 millimeters to about 12 millimeters, or another suitable range. In some embodiments, the saddle portion 136 may have a radial outer dimension SD or radial extent of about 2 millimeters to about 18 millimeters, about 4 millimeters to about 16 millimeters, about 8 millimeters to about 15 millimeters, or another suitable range. Other configurations are also contemplated.

The body portion 140 may have a plurality of body cells 142. The body portion 140 may include one or more filaments 144 interwoven around the central longitudinal axis of the endoprosthesis 100 and/or the expandable framework. In at least some embodiments, the body portion 140 may be coaxial with the anchoring portion 120. The one or more filaments 144 of the body portion 140 may form and/or define the plurality of body cells 142. The body portion 140 may be substantially tubular and/or may include a lumen extending axially through the body portion 140. The body portion 140 and/or the one or more filaments 144 interwoven around the central longitudinal axis of the endoprosthesis 100 and/or the expandable framework may define the lumen extending axially through the body portion 140. In at least some embodiments, the lumen extending axially through the body portion 140 may be aligned with, may be coaxial with, and/or may intersect with the lumen extending axially through the anchoring portion 120 to define a single lumen extending axially through the endoprosthesis 100 and/or the expandable framework.

In some embodiments, the body portion 140 may have an axial length BL of about 40 millimeters to about 150 millimeters, about 50 millimeters to about 135 millimeters, about 60 millimeters to about 120 millimeters, about 80 millimeters to about 100 millimeters, or another suitable range. In some embodiments, the body portion 140 may have a radial outer dimension BD or radial extent of about 5 millimeters to about 18 millimeters, about 6 millimeters to about 15 millimeters, about 8 millimeters to about 12 millimeters, or another suitable range. Other configurations are also contemplated.

In at least some embodiments, the anchoring portion 120 may be braided or woven from the one or more filaments 124. In at least some embodiments, the body portion 140 may be braided or woven from the one or more filaments 144. Other configurations for the anchoring portion 120 and/or the body portion 140 are also contemplated. In some embodiments, the anchoring portion 120 may have a denser configuration of filaments and/or smaller cells than the body portion 140. In some embodiments, the one or more filaments 124 of the anchoring portion 120 may have a smaller filament diameter or outer extent than the one or more filaments 144 of the body portion 140. In some embodiments, the anchoring portion 120 and the body portion 140 may be integrally formed as a unitary and/or monolithic structure. In some embodiments, the anchoring portion 120 and the body portion 140 may be separately formed and later joined and/or fixedly attached together, such as by welding, adhesive bonding, mechanical fixation, or other suitable means. In some embodiments, the one or more filaments 124 of the anchoring portion 120 may be the one or more filaments 144 of the body portion 140, or vice versa. For example, the entire endoprosthesis 100 and/or expandable framework may be formed from the same one or more filaments braided and/or interwoven together continuously as a single monolithic structure. Some suitable but non-limiting materials for the endoprosthesis 100, and/or components or elements thereof, for example metallic materials and/or polymeric materials, are described below.

In some embodiments, the body portion 140 may include a window 150 through a side and/or side wall of the body portion 140. The window 150 may be positioned adjacent the anchoring portion 120. In some embodiments, the body portion 140 may include a first body portion 146 opposite the window 150 relative to the central longitudinal axis of the endoprosthesis 100 and/or the expandable framework. In some embodiments, the body portion 140 may include a second body portion 148 opposite the anchoring portion 120 relative to the window 150.

In at least some embodiments, the window 150 may be formed by removing at least a portion of the one or more filaments 144 of the body portion 140. For example, the window 150 may be formed by cutting the one or more filaments 144 of the body portion 140. In some embodiments, the window 150 may occupy space equivalent to at least two of the plurality of body cells 142. In some embodiments, the window 150 may occupy space equivalent to at least 10 or more, at least 15 or more, at least 20 or more, etc. of the plurality of body cells 142. Other configurations are also contemplated. In some embodiments, the one or more filaments 144 may define a perimeter 152 of the window 150, wherein the one or more filaments 144 surround the window 150. In some embodiments, the perimeter 152 of the window 150 is at least partially defined by a plurality of welds 154 joining the one or more filaments 144 of the body portion 140 together. In some embodiments, the one or more filaments 144 of the body portion 140 may be welded or otherwise joined together prior to cutting the one or more filaments 144 of the body portion 140 to form the window 150. In some embodiments, welding the one or more filaments 144 of the body portion 140 together may also and/or simultaneously cut the one or more filaments 144 of the body portion 140 thereby forming the perimeter 152 of the window 150.

In some embodiments, the window 150 may have an axial length WL of about 15 to about 50 millimeters, about 20 to about 35 millimeters, or another suitable range. In some embodiments, the window 150 may have a circumferential opening dimension of about 20%, about 30%, about 40%, about 50%, about 60%, or about 70% of an overall circumference of the body portion 140. For example, in some embodiments, the circumferential opening dimension of the window 150 may be from about 40% to about 60% of the overall circumference of the body portion 140. Other configurations are also contemplated.

In some embodiments, the body portion 140 may include a flared end opposite the anchoring portion 120. In some embodiments, the flared end of the body portion 140 opposite the anchoring portion 120 may have a greater outer diameter and/or outer extent than a remainder of the body portion 140. In at least some embodiments, the flared end of the body portion 140 opposite the anchoring portion 120 may have an outer diameter and/or outer extent that is less than the radial outer dimension FD or radial extent of the first transverse flange 132 and/or the second transverse flange 134 of the anchoring portion 120. Alternatively, in some embodiments, the flared end of the body portion 140 opposite the anchoring portion 120 may have an outer diameter and/or outer extent that is greater than and/or similar to the radial outer dimension FD or radial extent of the first transverse flange 132 and/or the second transverse flange 134 of the anchoring portion 120.

Figure 3:
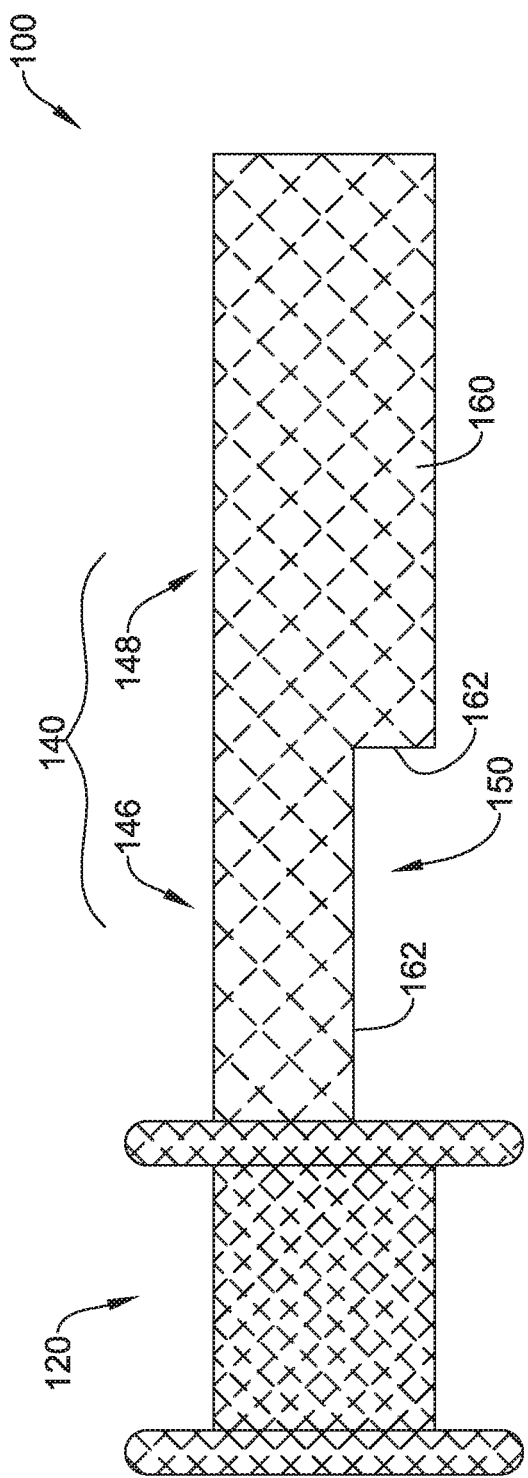
FIG. 3 illustrates the example endoprosthesis of FIG. 2 including a polymeric cover.

As seen in FIG. 3, the endoprosthesis 100 may include a polymeric cover 160 disposed on at least a portion of the expandable framework. In some embodiments, the polymeric cover 160 may be disposed on the anchoring portion 120. In some embodiments, the polymeric cover 160 may be disposed on the body portion 140. In some embodiments, the polymeric cover 160 may be disposed on both the anchoring portion 120 and the body portion 140. In some embodiments, the polymeric cover 160 may be disposed on and/or along an outer surface of the expandable framework. In some embodiments, the expandable framework (e.g., the anchoring portion 120 and/or the body portion 140) may be embedded in the polymeric cover 160. In some embodiments, the polymeric cover 160 may be fixedly or releasably secured to, bonded to, or otherwise attached to expandable framework (e.g., the anchoring portion 120 and/or the body portion 140). In some embodiments, the polymeric cover 160 may further join and/or fixedly attached the body portion 140 to the anchoring portion 120. In some embodiments, the polymeric cover 160 alone may join and/or fixedly attached the body portion 140 to the anchoring portion 120.

In some embodiments, the polymeric cover 160 may be impermeable to fluids, debris, medical instruments, etc. The window 150 may be devoid of the polymeric cover 160 and any other structure within the perimeter 152 of the window 150. As such, the window 150 may be configured to permit unobstructed passage of fluids, debris, medical instruments, etc. through the side and/or side wall of the body portion 140 of the endoprosthesis 100 and/or the expandable framework within the perimeter 152 of the window 150. In some embodiments, the perimeter 152 of the window 150 is at least partially defined by one or more edges 162 of the polymeric cover 160. In some embodiments, the polymeric cover 160 may be coincident with and/or may align with the one or more filaments 144 of the body portion 140 defining the perimeter 152 of the window 150. In some embodiments, the one or more edges 162 of the polymeric cover 160 may terminate at the one or more filaments 144 of the body portion 140 defining the perimeter 152 of the window 150. In some embodiments, the one or more edges 162 of the polymeric cover 160 may extend between adjacent welds 154 and/or may extend between adjacent filaments 144. Some suitable but non-limiting materials for the polymeric cover 160 are described below.

Figure 4:
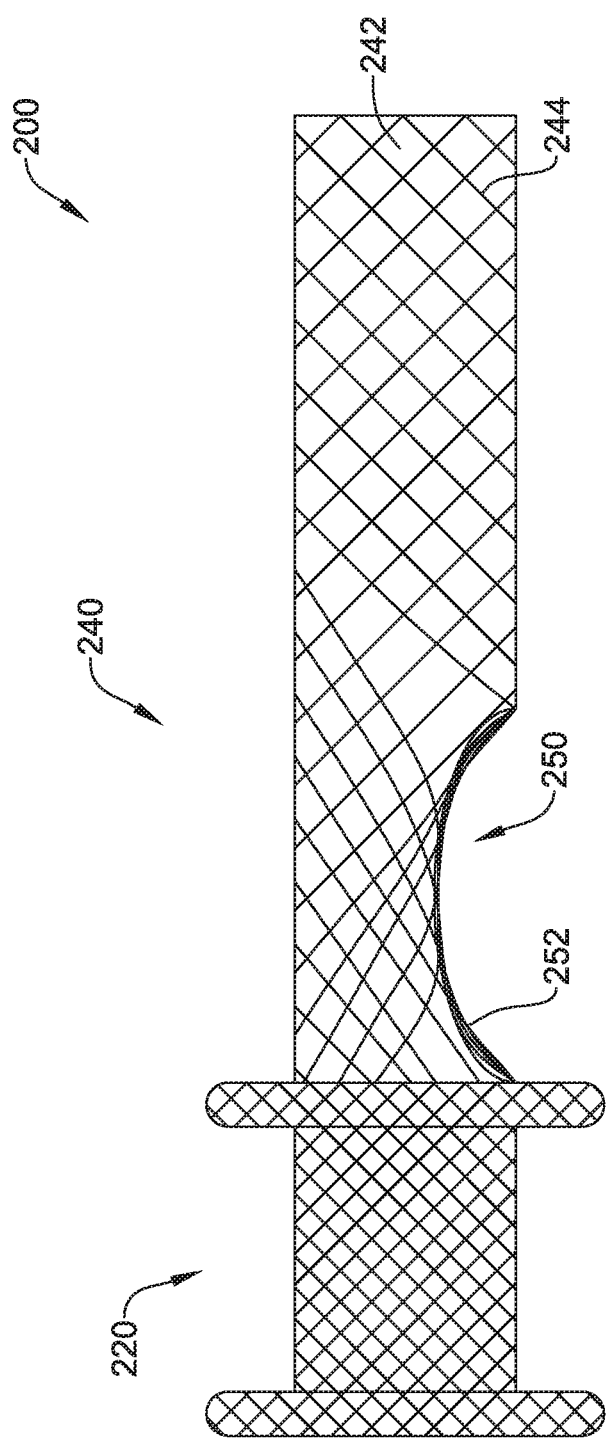
FIG. 4 illustrates an alternative construction of the example endoprosthesis of FIG. 2.

FIG. 4 illustrates an example endoprosthesis 200, which is similar in form and construction to the endoprosthesis 100, except as discussed herein. The endoprosthesis 200 may include an anchoring portion 220 and a body portion 240 extending axially from the anchoring portion 220. In some embodiments, the anchoring portion 220 may be braided or woven from one or more filaments. In some embodiments, the body portion 240 may be braided or woven from one or more filaments 244. The body portion 240 may have a plurality of body cells 242 defined by the one or more filaments 244. The body portion 240 may include a window 250 through a side and/or side wall of the body portion 240. The window 250 may be positioned adjacent the anchoring portion 220. In one difference from the window 150 and the body portion 140 above, the window 250 may be formed without cutting and/or welding (or otherwise joining) any of the one or more filaments 244 of the body portion 240. Instead, the one or more filaments 244 may each be arranged and/or may extend around a perimeter 252 of the window 250 such that multiple filaments of the one or more filaments 244 may define the perimeter 252 of the window 250. For example, when braiding and/or weaving the one or more filaments 244 of the body portion 240, a braiding mandrel may include a raised portion or a protrusion that the one or more filaments 244 are directed around to form the perimeter 252 of the window 250. As such, the raised portion or the protrusion of the mandrel effectively defines the window 250 when the endoprosthesis 200 is disposed on the braiding mandrel.

As may be seen in FIG. 4, as the one or more filaments 244 approach the window 250, the pitch between adjacent filaments may be altered to angle the one or more filaments 244 around the perimeter 252 of the window 250. As such, the pitch between adjacent filaments may be variable along the axial length of the body portion 240, with the pitch between adjacent filaments being widest adjacent axial ends of the window 250. Accordingly, the plurality of body cells 242 may be variable in size, with the plurality of body cells 242 formed by the filaments having the widest pitch generally being the largest. Regardless of the size of any individual cell of the plurality of body cells 242, the window 250 may still occupy space equivalent to at least of the plurality of body cells 242. Additionally, similar to the endoprosthesis 100 above, the endoprosthesis 200 may include a polymeric cover (not shown) arranged and/or configured as discussed above. Some suitable but non-limiting materials for the endoprosthesis 200, and/or components or elements thereof, for example metallic materials and/or polymeric materials, are described below.

Figure 5:
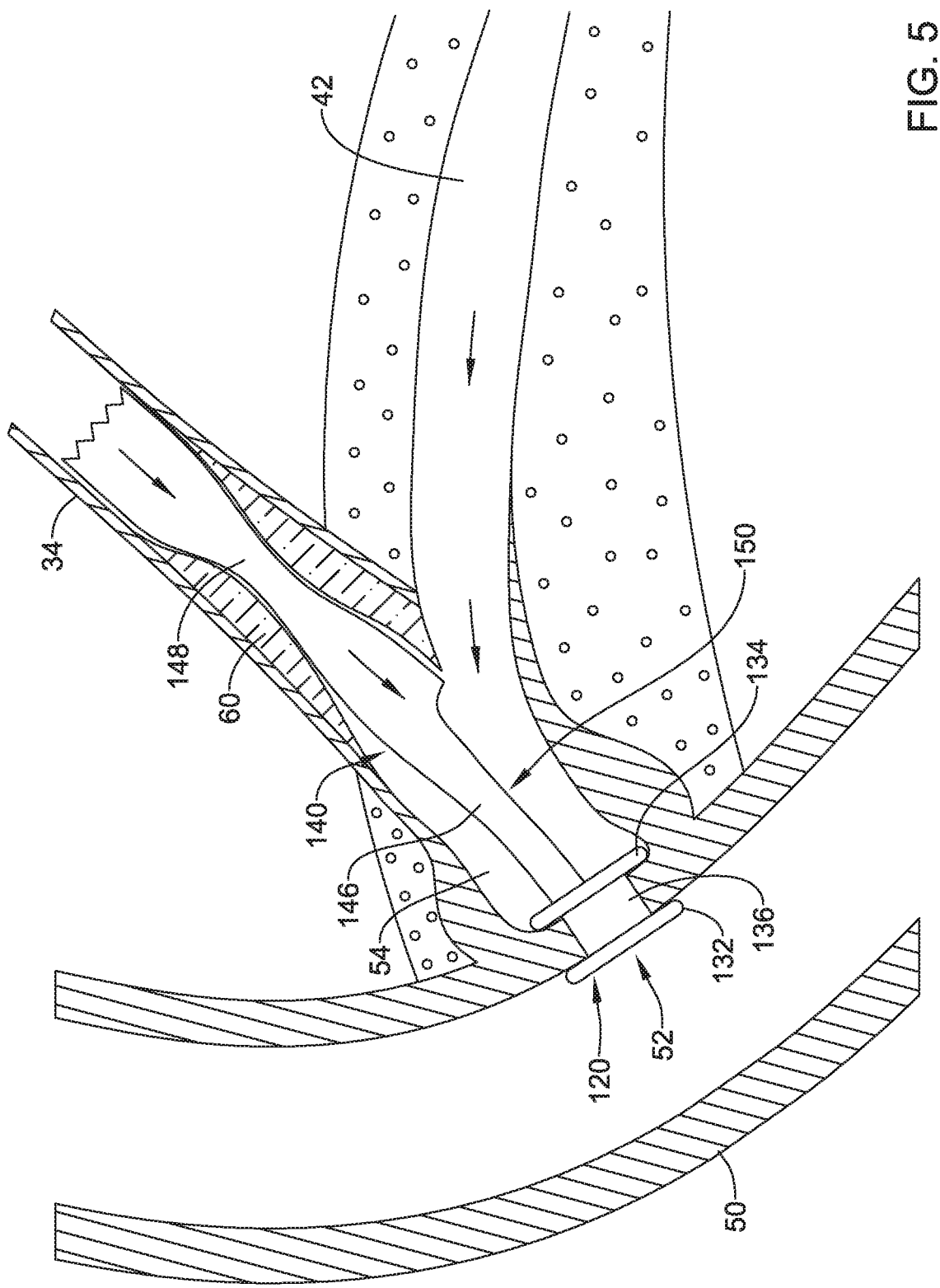
FIG. 5 illustrates an example placement of the endoprosthesis of FIGS. 2-4 in the patient's biliary tree.
Figure 6:
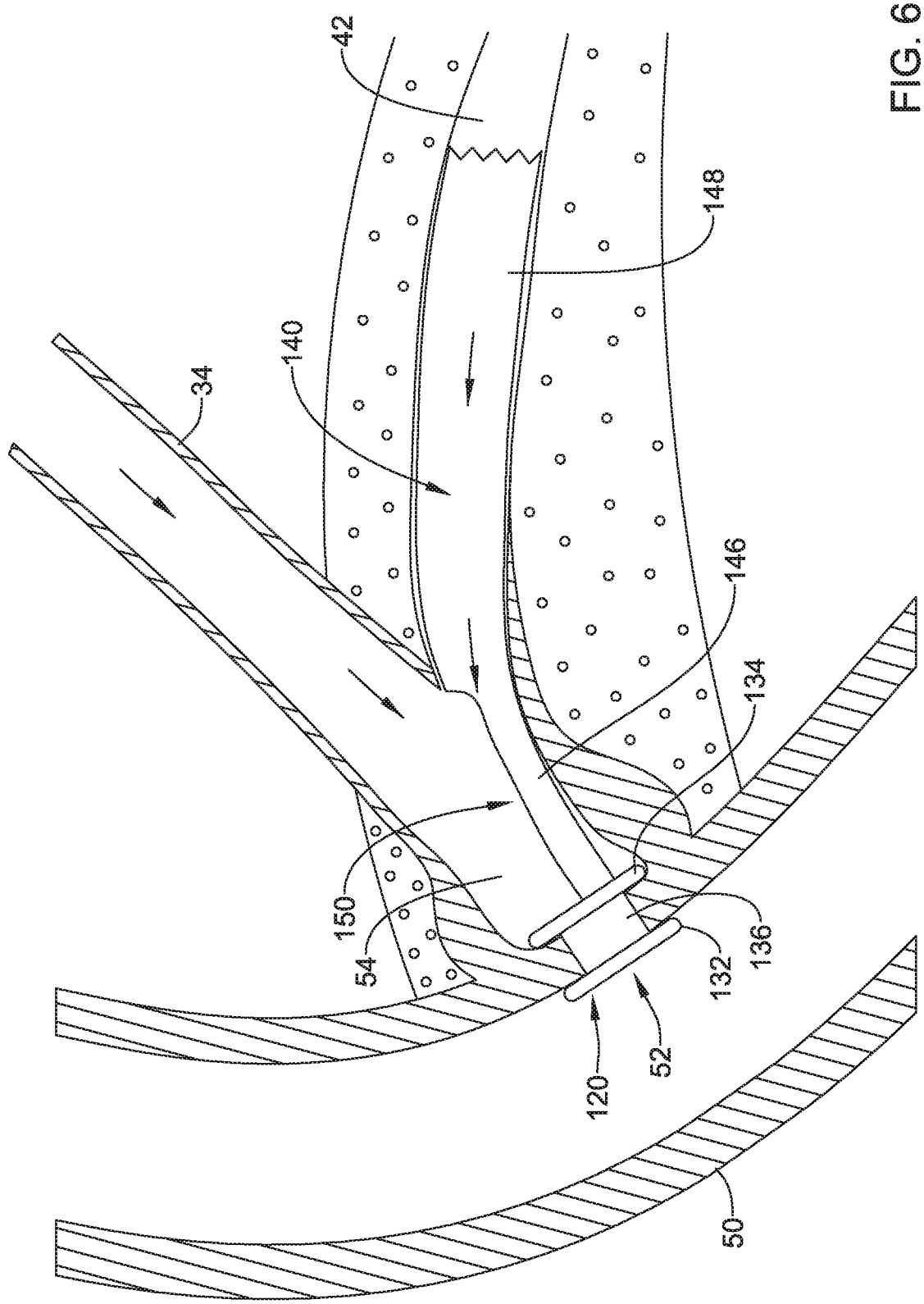
FIG. 6 illustrates an example placement of the endoprosthesis of FIGS. 2-4 in the patient's biliary tree.

In the endoprosthesis 100 (and similarly the endoprosthesis 200), the first and second transverse flanges 132/134 may be configured to and/or may cooperate to secure the anchoring portion 120 at an orifice of a body lumen, such as the papilla of Vater 52. In the deployed configuration, the first transverse flange 132 and the second transverse flange 134 may be configured to sandwich, pinch, and/or compress tissue forming the orifice of the body lumen therebetween. For example, the first transverse flange 132 may be configured to be positioned outside of the body lumen (e.g., within the duodenum 50) and the second transverse flange 134 may be configured to be positioned inside of the body lumen (e.g., within the ampulla of Vater 54) on an opposite side of the tissue forming the orifice of the body lumen (e.g., the papilla of Vater 52) with the saddle portion 136 extending through and/or disposed within the orifice of the body lumen (e.g., within and/or extending through the papilla of Vater 52), as seen in FIGS. 5 and 6 for example. The first transverse flange 132 and the second transverse flange 134 may prevent migration of the endoprosthesis 100 within the body lumen and/or within or through the orifice of the body lumen (e.g., the papilla of Vater 52).

The body portion 140 may extend axially away from the anchoring portion 120 and into the body lumen being treated. In one example, the body lumen (e.g., the common bile duct 34 and/or the pancreatic duct 42) may be partially and/or completely obstructed by a stricture 60, as seen in FIG. 5. The body portion 140 may be disposed within the body lumen extending through the stricture 60 to maintain and/or re-establish patency of the body lumen. In some embodiments, the body portion 140 may be configured to dilate at least a portion of the body lumen in the deployed configuration. For example, the body portion 140 may be configured to exert a radially outward force upon a wall of the body lumen (e.g., the common bile duct 34 and/or the pancreatic duct 42) and/or against the stricture 60 that has formed therein.

In some embodiments, the window 150 may result in a reduced radially outward force being applied to the wall of the body lumen in the first body portion 146 due to the body portion 140 having an incomplete circumference along the axial length of the window 150. In some embodiments, the first body portion 146 opposite the window 150 relative to the central longitudinal axis of the endoprosthesis 100 and/or the expandable framework and may be configured to exert less radially outward force on the body lumen than the second body portion 148 opposite the anchoring portion 120 relative to the window 150. For example, in the arrangement shown in FIG. 5, the first body portion 146 may be positioned within the ampulla of Vater 54, and may be configured to exert less radially outward force on the ampulla of Vater 54 than the second body portion 148 exerts on the common bile duct 34 and/or the stricture 60, which has partially obstructed the common bile duct 34.

The endoprosthesis 100 may be oriented using a suitable imaging technique or other means such that the window 150 faces toward an opening of an adjacent and/or branching body lumen. In the example of FIG. 5, the body portion 140 extends into the common bile duct 34 and the window 150 faces toward the opening of the pancreatic duct 42. This orientation permits fluid and/or debris within the common bile duct 34 to flow through the lumen of the body portion 140 and/or past the stricture 60 without obstructing the pancreatic duct 42. Similarly, the same endoprosthesis 100 may be positioned with the body portion 140 extending within the pancreatic duct 42 and the window 150 facing toward the opening of the common bile duct 34, as seen in FIG. 6. This orientation permits fluid and/or debris within the pancreatic duct 42 to flow through the lumen of the body portion 140 (and/or past any structure that may have formed within the pancreatic duct 42) without obstructing the common bile duct 34. Accordingly, in both examples, fluids and/or debris from both body lumens may flow through the lumen of the anchoring portion 120 and/or the through the papilla of Vater 52 and into the duodenum 50.

Figure 7:
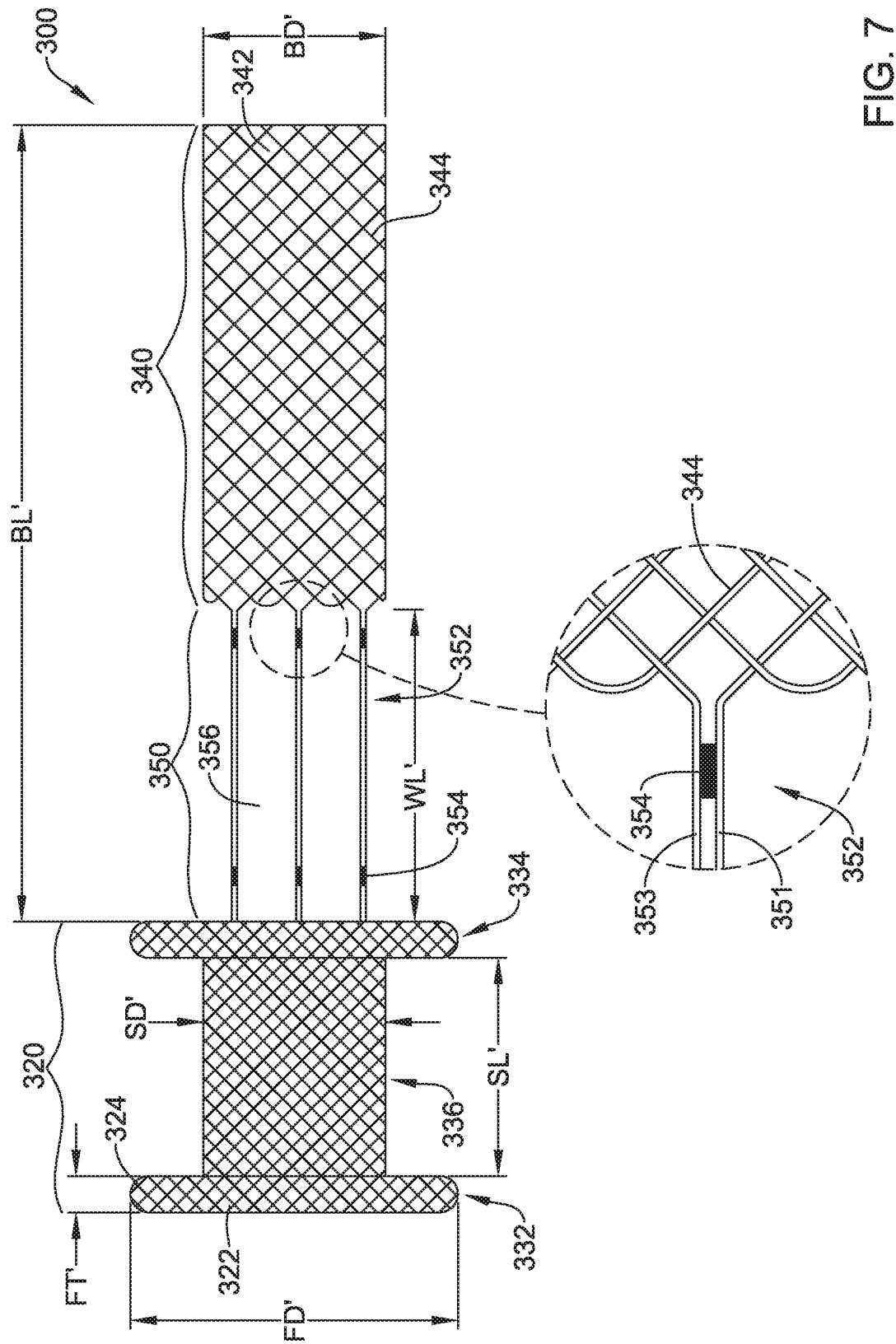
FIG. 7 illustrates aspects of an example endoprosthesis.

FIG. 7 illustrates an example endoprosthesis 300 (which term may be used interchangeably with the term "stent" herein) comprising an expandable framework including an anchoring portion 320, a body portion 340 extending axially away from the anchoring portion 320 along a central longitudinal axis of the endoprosthesis 300 and/or the expandable framework, and a linking portion 350 extending axially from the anchoring portion 320 to the body portion 340 along the central longitudinal axis of the endoprosthesis 300 and/or the expandable framework. The endoprosthesis 300 and/or the expandable framework may be configured to shift between a delivery configuration and a deployed configuration. The delivery configuration may be axially elongated and/or radially collapsed or compressed compared to the deployed configuration. The deployed configuration may be axially shortened and/or radially expanded compared to the delivery configuration. In at least some embodiments, the endoprosthesis 300 and/or the expandable framework may be self-expandable. For example, the endoprosthesis 300 and/or the expandable framework may be formed from a shape memory material. In some embodiments, the endoprosthesis 300 and/or the expandable framework may be mechanically expandable. For example, the endoprosthesis 300 and/or the expandable framework may be expandable using an inflatable balloon, using an actuation member, or other suitable means. During delivery to a treatment site, the endoprosthesis 300 and/or the expandable framework may be disposed within a lumen of a delivery sheath in the delivery configuration. Upon removal from the lumen of the delivery sheath, the endoprosthesis 300 and/or the expandable framework may be shifted to the deployed configuration.

As seen in the deployed configuration illustrated in FIG. 7, the anchoring portion 320 may have a plurality of anchoring cells 322. The anchoring portion 320 may include one or more filaments 324 interwoven around the central longitudinal axis of the endoprosthesis 300 and/or the expandable framework. The one or more filaments 324 of the anchoring portion 320 may form and/or define the plurality of anchoring cells 322. In the deployed configuration, the anchoring portion 320 may include a first transverse flange 332 and a second transverse flange 334 proximate the first transverse flange 332. The anchoring portion 320 may be substantially tubular and/or may include a lumen extending axially through the anchoring portion 320. The first transverse flange 332 and the second transverse flange 334 may be axially spaced apart by a saddle portion 336. In some embodiments, the saddle portion 336 may substantially define the lumen extending axially through the anchoring portion 320.

In some embodiments, the first transverse flange 332 and/or the second transverse flange 334 may each have an axial thickness FT' or axial extent of about 0.5 millimeters to about 3 millimeters, about 1 millimeter to about 2 millimeters, or another suitable range. In some embodiments, the first transverse flange 332 and/or the second transverse flange 334 may each have a radial outer dimension FD' or radial extent of about 15 millimeters to about 30 millimeters, about 17 millimeters to about 24 millimeters, about 18 millimeters to about 20 millimeters, or another suitable range. In some embodiments, the saddle portion 336 may have an axial length SL' of about 2 millimeters to about 18 millimeters, about 5 millimeters to about 15 millimeters, about 8 millimeters to about 12 millimeters, or another suitable range. In some embodiments, the saddle portion 336 may have a radial outer dimension SD' or radial extent of about 2 millimeters to about 18 millimeters, about 4 millimeters to about 16 millimeters, about 8 millimeters to about 15 millimeters, or another suitable range. Other configurations are also contemplated.

The body portion 340 may have a plurality of body cells 342. The body portion 340 may include one or more filaments 344 interwoven around the central longitudinal axis of the endoprosthesis 300 and/or the expandable framework. In at least some embodiments, the body portion 340 may be coaxial with the anchoring portion 320 and/or the linking portion 350. The one or more filaments 344 of the body portion 340 may form and/or define the plurality of body cells 342. The body portion 340 may be substantially tubular and/or may include a lumen extending axially through the body portion 340. The body portion 340 and/or the one or more filaments 344 interwoven around the central longitudinal axis of the endoprosthesis 300 and/or the expandable framework may define the lumen extending axially through the body portion 340. In at least some embodiments, the lumen extending axially through the body portion 340 may be aligned with, may be coaxial with, and/or may intersect with the lumen extending axially through the anchoring portion 320 to define a single lumen extending axially through the endoprosthesis 300 and/or the expandable framework.

In some embodiments, the body portion 340 may have an axial length BL' of about 40 millimeters to about 150 millimeters, about 50 millimeters to about 135 millimeters, about 60 millimeters to about 120 millimeters, about 80 millimeters to about 100 millimeters, or another suitable range. In some embodiments, the body portion 340 may have a radial outer dimension BD' or radial extent of about 5 millimeters to about 18 millimeters, about 6 millimeters to about 15 millimeters, about 8 millimeters to about 12 millimeters, or another suitable range. Other configurations are also contemplated.

In some embodiments, the linking portion 350 may include a plurality of longitudinally-oriented struts 352 spacing the body portion 340 from the anchoring portion 320. The linking portion 350 may be positioned immediately adjacent the anchoring portion 320. The plurality of longitudinally-oriented struts 352 may include one or more pairs of a first strut 351 and a second strut 353 extending longitudinally from the anchoring portion 320 to the body portion 340. The first strut 351 and the second strut 353 may be positioned and/or oriented substantially parallel to each other. In at least some embodiments, the plurality of longitudinally-oriented struts 352, and/or the one or more pairs of the first strut 351 and the second strut 353, may be positioned and/or oriented substantially parallel to the central longitudinal axis of the endoprosthesis 300 and/or the expandable framework.

In some embodiments, the linking portion 350 and/or the plurality of longitudinally-oriented struts 352 may have an axial length WL' of about 15 to about 50 millimeters, about 20 to about 35 millimeters, or another suitable range. Other configurations are also contemplated. In at least some embodiments, the linking portion 350 and/or the plurality of longitudinally-oriented struts 352 may be axially longer than the anchoring portion 320 and/or axially shorter than the body portion 340.

In at least some embodiments, the linking portion 350 may be formed by manipulating at least a portion of the one or more filaments 344 of the body portion 340. For example, one of the one or more filaments 344 may extend away from the body portion 340 to form the first strut 351 and another of the one or more filaments 344 may extend away from the body portion 340 to form the second strut 353. In some embodiments, the first strut 351 and the second strut 353 may be fixedly attached together using one or more welds 354, or other suitable fixation means including but not limited to adhesive bonding, etc., disposed along and between the first strut 351 and the second strut 353 within the linking portion 350. In some embodiments, at least some of the one or more filaments 344 may be "turned back" at a proximal end of the body portion 340. In some embodiments, one or more of the "turned back" filaments may be disposed between adjacent pairs of the one or more pairs of the first strut 351 and the second strut 353. In some embodiments, a free end of the one or more "turned back" filaments may be fixedly attached (e.g., welded, bonded, etc.) to one or more of the one or more filaments 344 distal of the proximal end of the body portion 340 and/or within the body portion 340.

In some embodiments, the linking portion 350 define a plurality of longitudinally-extending openings 356 disposed between adjacent struts of the plurality of longitudinally-oriented struts 352. For example, one of the plurality of longitudinally-extending openings 356 may be disposed between the second strut 353 of one pair of the one or more pairs of the first strut 351 and the second strut 353 and the first strut 351 of an adjacent pair of the one or more pairs of the first strut 351 and the second strut 353. In some embodiments, each longitudinally-extending opening 356 may occupy space equivalent to at least two of the plurality of body cells 342. In some embodiments, each longitudinally-extending opening 356 may occupy space equivalent to at least 10 or more, at least 15 or more, at least 20 or more, etc. of the plurality of body cells 342. Other configurations are also contemplated.

In some embodiments, the body portion 340 may include a flared end opposite the anchoring portion 320. In some embodiments, the flared end of the body portion 340 opposite the anchoring portion 320 may have a greater outer diameter and/or outer extent than a remainder of the body portion 340. In at least some embodiments, the flared end of the body portion 340 opposite the anchoring portion 320 may have an outer diameter and/or outer extent that is less than the radial outer dimension FD' or radial extent of the first transverse flange 332 and/or the second transverse flange 334 of the anchoring portion 320. Alternatively, in some embodiments, the flared end of the body portion 340 opposite the anchoring portion 320 may have an outer diameter and/or outer extent that is greater than and/or similar to the radial outer dimension FD' or radial extent of the first transverse flange 332 and/or the second transverse flange 334 of the anchoring portion 320.

In at least some embodiments, the anchoring portion 320 may be braided or woven from the one or more filaments 324. In at least some embodiments, the body portion 340 may be braided or woven from the one or more filaments 344. Other configurations for the anchoring portion 320 and/or the body portion 340 are also contemplated. In some embodiments, the anchoring portion 320 may have a denser configuration of filaments and/or smaller cells than the body portion 340. In some embodiments, the one or more filaments 324 of the anchoring portion 320 may have a smaller filament diameter or outer extent than the one or more filaments 344 of the body portion 340. In some embodiments, the anchoring portion 320 and the body portion 340 may be integrally formed as a unitary and/or monolithic structure. In some embodiments, the anchoring portion 320 and the body portion 340 may be separately formed and later joined and/or fixedly attached together, such as by welding, adhesive bonding, mechanical fixation, or other suitable means. In some embodiments, the one or more filaments 324 of the anchoring portion 320 may be the one or more filaments 344 of the body portion 340, or vice versa. For example, the entire endoprosthesis 300 and/or expandable framework may be formed from the same one or more filaments braided and/or interwoven together continuously as a single monolithic structure. Some suitable but non-limiting materials for the endoprosthesis 300, and/or components or elements thereof, for example metallic materials and/or polymeric materials, are described below.

Figure 8:
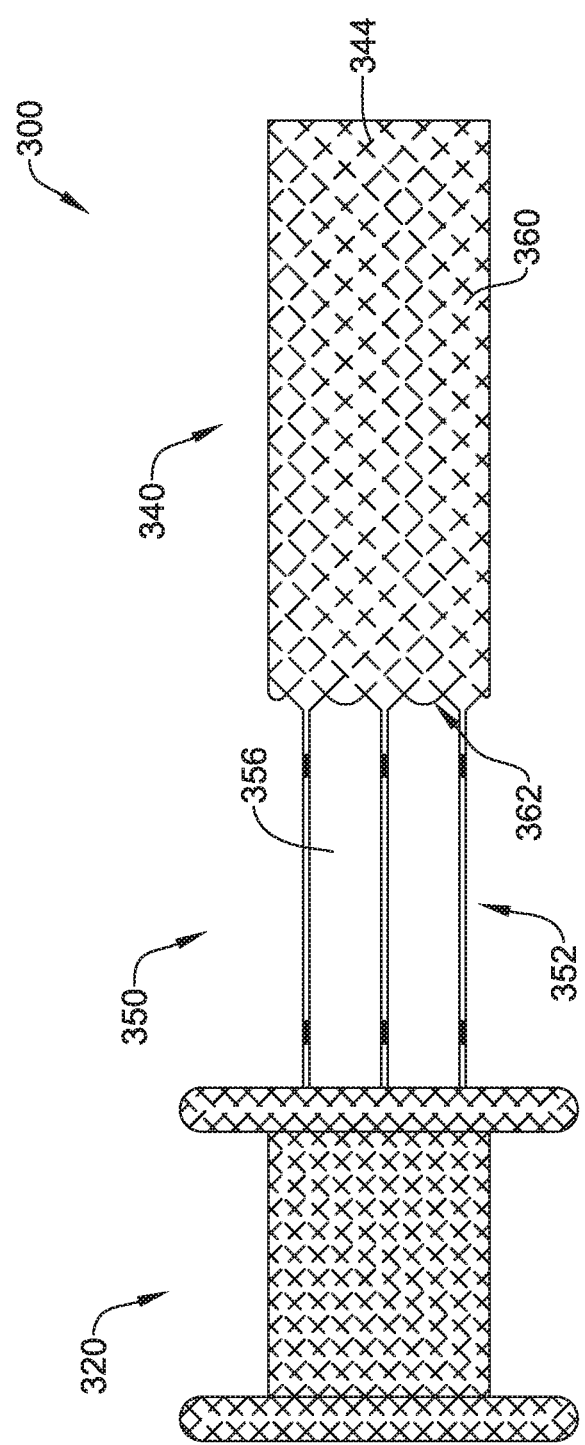
FIG. 8 illustrates the example endoprosthesis of FIG. 7 including a polymeric cover.

As seen in FIG. 8, the endoprosthesis 300 may include a polymeric cover 360 disposed on at least a portion of the expandable framework. In some embodiments, the polymeric cover 360 may be disposed on the anchoring portion 320. In some embodiments, the polymeric cover 360 may be disposed on the body portion 340. In some embodiments, the polymeric cover 360 may be disposed on both the anchoring portion 320 and the body portion 340. In some embodiments, the polymeric cover 360 may be disposed on and/or along an outer surface of the expandable framework. In some embodiments, the expandable framework (e.g., the anchoring portion 320 and/or the body portion 340) may be embedded in the polymeric cover 360. In some embodiments, the polymeric cover 360 may be fixedly or releasably secured to, bonded to, or otherwise attached to expandable framework (e.g., the anchoring portion 320 and/or the body portion 340).

In some embodiments, the polymeric cover 360 may be impermeable to fluids, debris, medical instruments, etc. The linking portion 350 may be devoid of the polymeric cover 360. As such, the linking portion 350 may be configured to permit unobstructed passage of fluids, debris, etc. through the side and/or side wall of the body portion 340 of the endoprosthesis 300 and/or the expandable framework within the linking portion 350. In some embodiments, the linking portion 350 is at least partially defined by one or more edges 362 of the polymeric cover 360. In some embodiments, the polymeric cover 360 may be coincident with and/or may align with the one or more filaments 344 of the body portion 340 defining a distal end of the linking portion 350 and/or the proximal end of the body portion 340. In some embodiments, the one or more edges 362 of the polymeric cover 360 may terminate at the one or more filaments 344 of the body portion 340 defining the distal end of the linking portion 350. In some embodiments, the one or more edges 362 of the polymeric cover 360 may extend between adjacent filaments 344. Some suitable but non-limiting materials for the polymeric cover 360 are described below.

Figure 9:
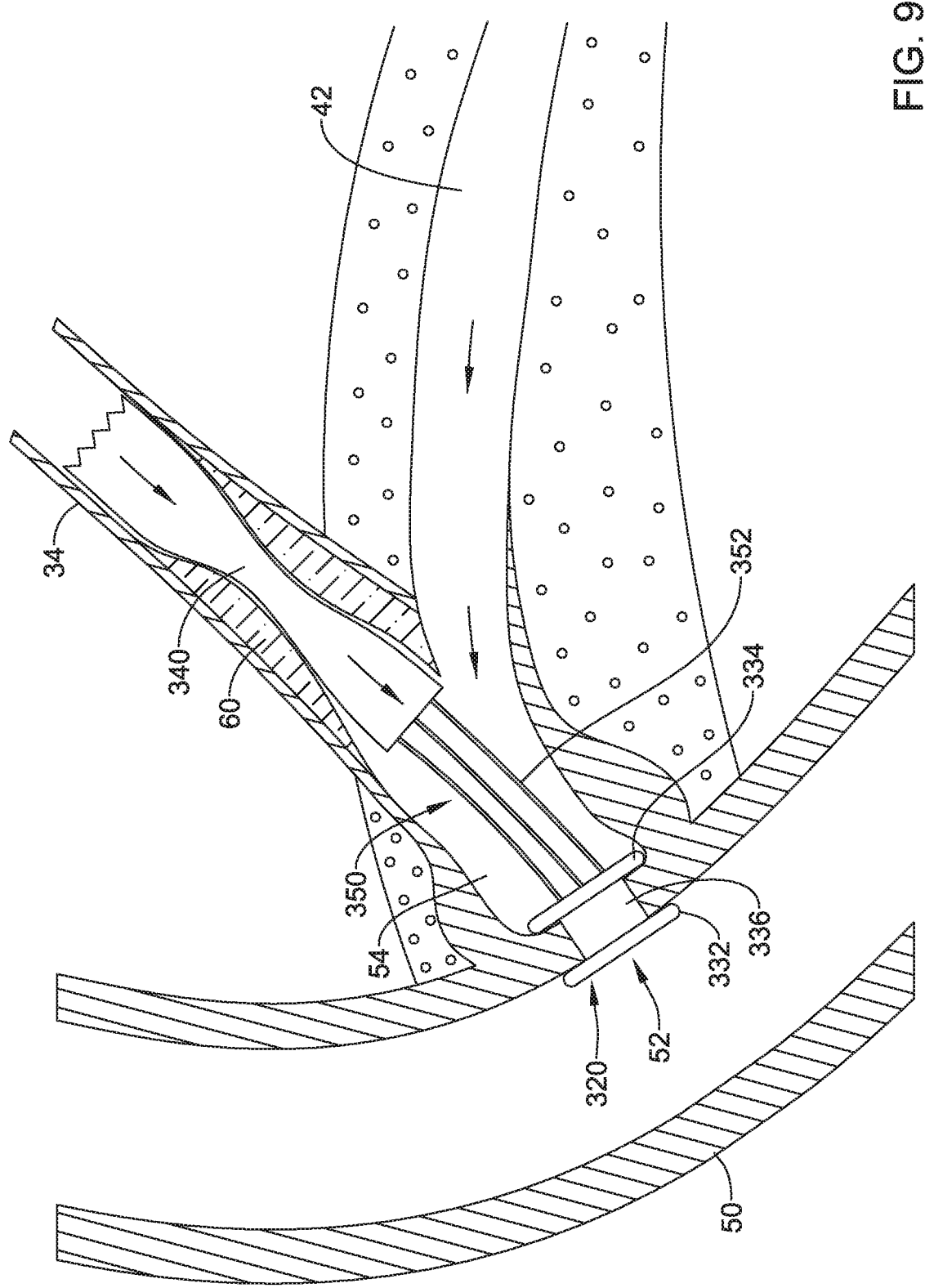
FIG. 9 illustrates an example placement of the endoprosthesis of FIGS. 7-8 in the patient's biliary tree.
Figure 10:
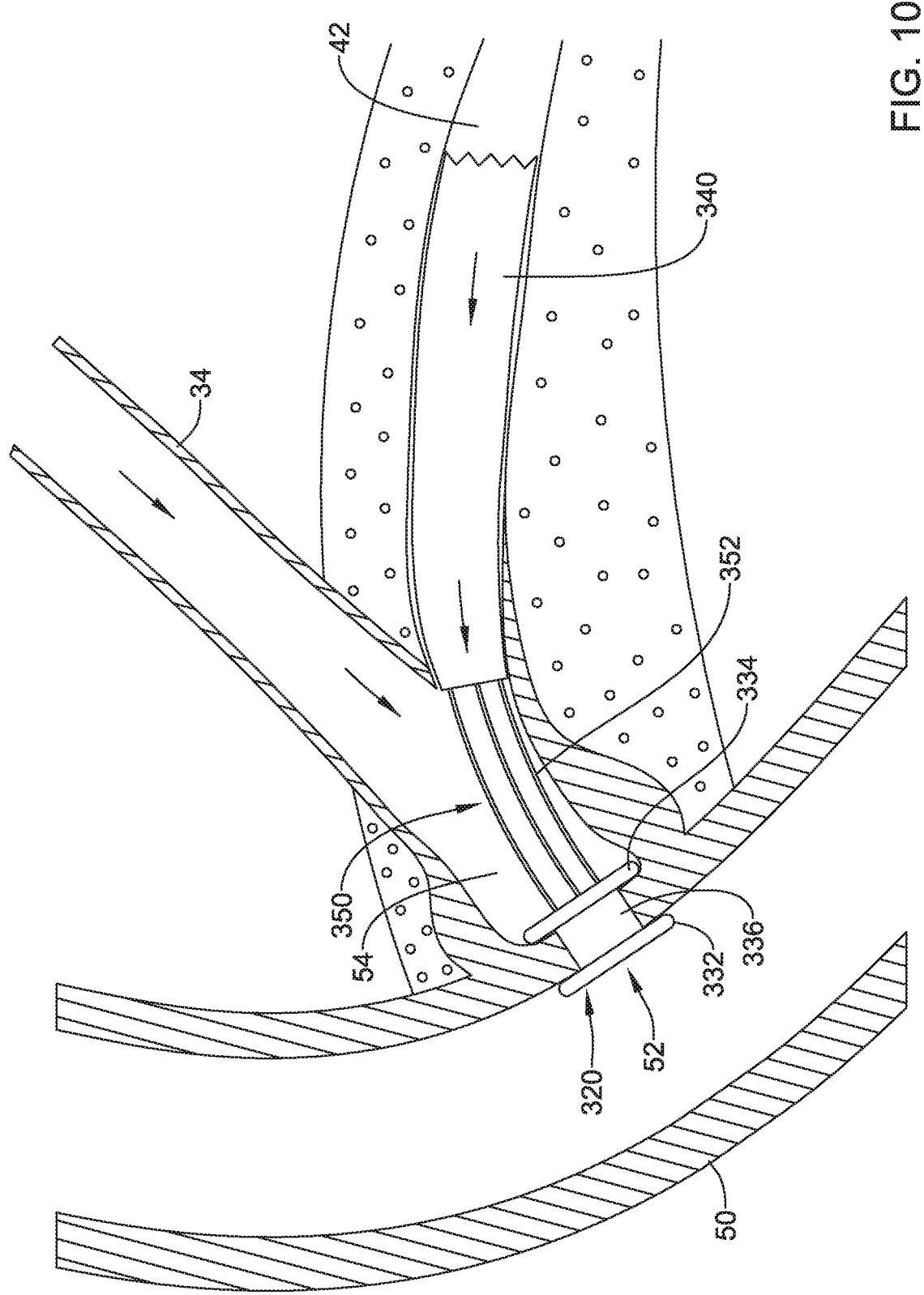
FIG. 10 illustrates an example placement of the endoprosthesis of FIGS. 7-8 in the patient's biliary tree.

In the endoprosthesis 300, the first and second transverse flanges 332/334 may be configured to and/or may cooperate to secure the anchoring portion 320 at an orifice of a body lumen, such as the papilla of Vater 52. In the deployed configuration, the first transverse flange 332 and the second transverse flange 334 may be configured to sandwich, pinch, and/or compress tissue forming the orifice of the body lumen therebetween. For example, the first transverse flange 332 may be configured to be positioned outside of the body lumen (e.g., within the duodenum 50) and the second transverse flange 334 may be configured to be positioned inside of the body lumen (e.g., within the ampulla of Vater 54) on an opposite side of the tissue forming the orifice of the body lumen (e.g., the papilla of Vater 52) with the saddle portion 336 extending through and/or disposed within the orifice of the body lumen (e.g., within and/or extending through the papilla of Vater 52), as seen in FIGS. 9 and 10 for example. The first transverse flange 332 and the second transverse flange 334 may prevent migration of the endoprosthesis 300 within the body lumen and/or within or through the orifice of the body lumen (e.g., the papilla of Vater 52).

The body portion 340 may extend axially away from the anchoring portion 320 and into the body lumen being treated. In one example, the body lumen (e.g., the common bile duct 34 and/or the pancreatic duct 42) may be partially and/or completely obstructed by a stricture 60, as seen in FIG. 9. The body portion 340 may be disposed within the body lumen extending through the stricture 60 to maintain and/or re-establish patency of the body lumen. In some embodiments, the body portion 340 may be configured to dilate at least a portion of the body lumen in the deployed configuration. For example, the body portion 340 may be configured to exert a radially outward force upon a wall of the body lumen (e.g., the common bile duct 34 and/or the pancreatic duct 42) and/or against the stricture 60 that has formed therein.

In some embodiments, the linking portion 350 may be configured to exert less radially outward force on the body lumen than the body portion 340. For example, in the arrangement shown in FIG. 9, the linking portion 350 may be positioned within the ampulla of Vater 54, and may be configured to exert less radially outward force on the ampulla of Vater 54 than the body portion 340 exerts on the common bile duct 34 and/or the stricture 60, which has partially obstructed the common bile duct 34.

The endoprosthesis 300 may be positioned using a suitable imaging technique or other means such that the linking portion 350 extends across an opening of an adjacent and/or branching body lumen. In the example of FIG. 9, the body portion 140 extends into the common bile duct 34 and the linking portion 350 extends across the opening of the pancreatic duct 42. This positioning permits fluid and/or debris within the common bile duct 34 to flow through the lumen of the body portion 140 and/or past the stricture 60 without obstructing the pancreatic duct 42. Similarly, the same endoprosthesis 300 may be positioned with the body portion 340 extending within the pancreatic duct 42 and linking portion 350 extending across the opening of the common bile duct 34, as seen in FIG. 10. This positioning permits fluid and/or debris within the pancreatic duct 42 to flow through the lumen of the body portion 340 (and/or past any structure that may have formed within the pancreatic duct 42) without obstructing the common bile duct 34. Accordingly, in both examples, fluids and/or debris from both body lumens may flow through the lumen of the anchoring portion 320 and/or the through the papilla of Vater 52 and into the duodenum 50. Since the orientation of the endoprosthesis 300 is non-directional, placement in a particular orientation is not necessary in order to obtain the benefit(s) of the linking portion 350 extending across the opening of an adjacent and/or branching body lumen, which may reduce procedure time and cost as well as reduce orientation errors that could result in a blocked or partially blocked adjacent and/or branching body lumen.

Figure 11:
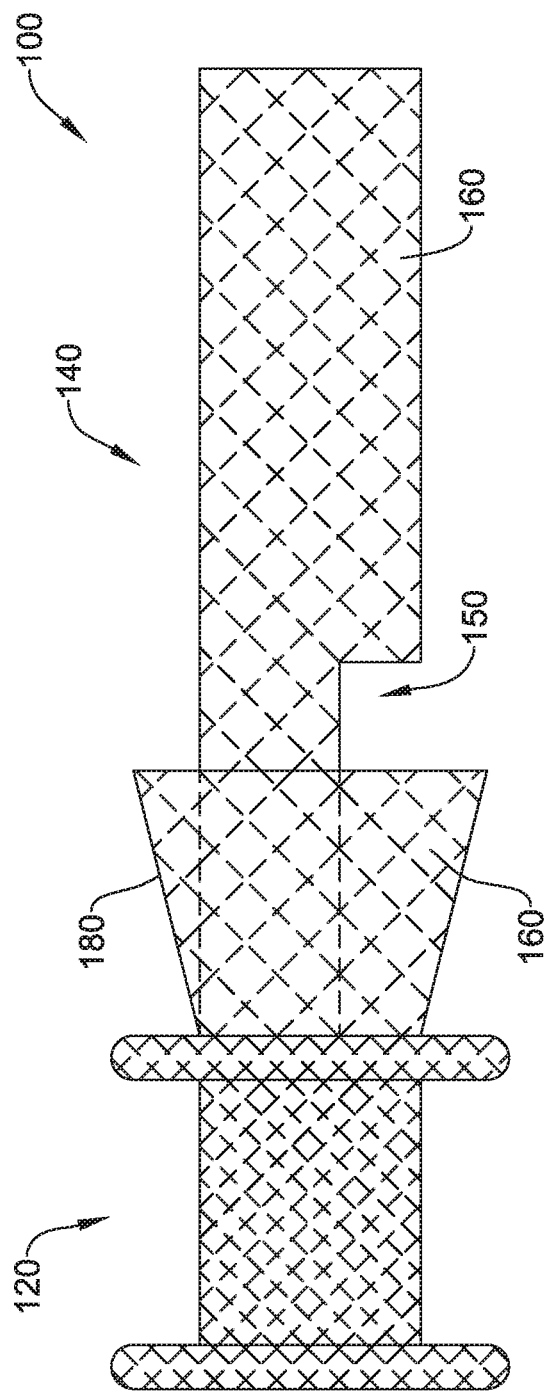
FIG. 11 illustrates aspects of an example endoprosthesis.

In an alternative configuration, the expandable framework of the endoprosthesis 100 of FIG. 2 may further include a tapered flange 180 extending axially away from the anchoring portion 120 and radially outward from the body portion 140, as seen in FIG. 11. For example, the tapered flange 180 may extend distally from the anchoring portion 120 toward and/or coaxially with the body portion 140. In some embodiments, the tapered flange 180 may at least partially axially overlap the window 150. In at least some embodiments, the polymeric cover 160 may be disposed on the tapered flange 180. In some embodiments, the tapered flange 180 may be embedded within the polymeric cover 160. When the endoprosthesis 100 is placed within the body lumen, the tapered flange 180 may be configured to direct and/or funnel fluid and/or debris from the adjacent and/or branching body lumen into the lumen of the anchoring portion 120. For example, the tapered flange 180 could be deployed within the ampulla of Vater 54 and the tapered flange 180 may be configured to engage with and/or exert a radially outward force against the wall of the body lumen (e.g., the ampulla of Vater 54). While not explicitly illustrated, the tapered flange 180 of the endoprosthesis 100 may also be implemented in connection with the endoprosthesis 200 in a similar manner to that described with respect to the endoprosthesis 100.

Figure 12:
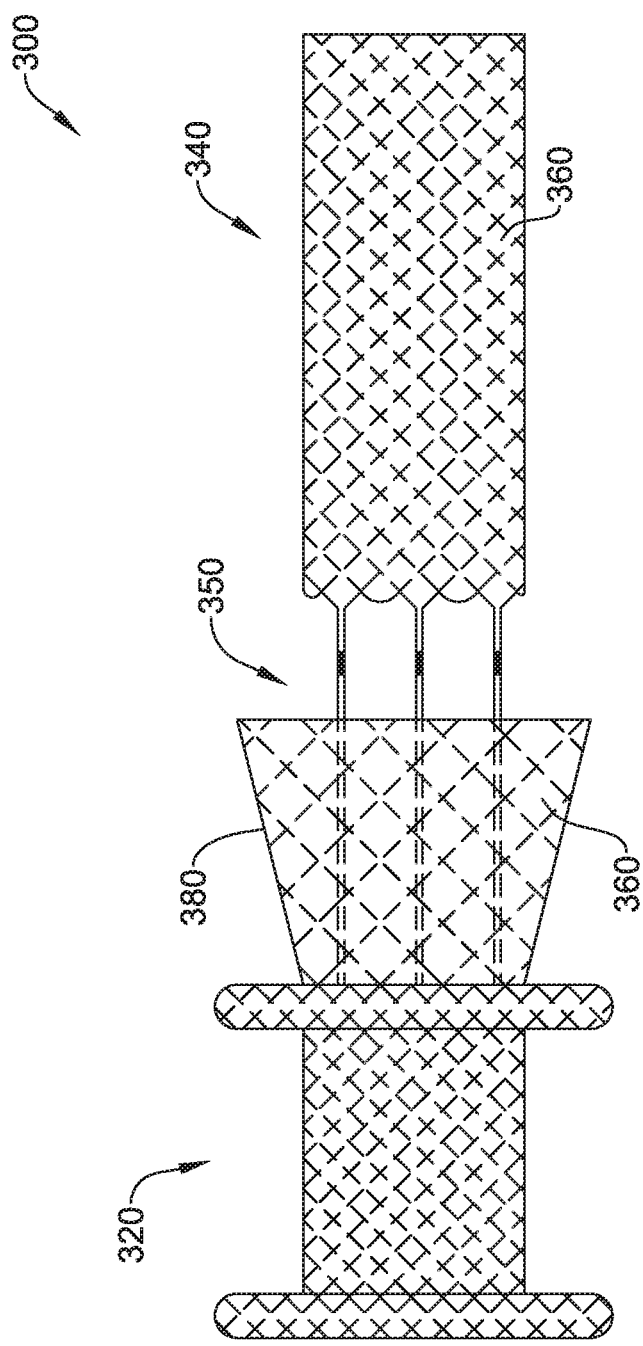
FIG. 12 illustrates aspects of an example endoprosthesis.

In another alternative configuration, the expandable framework of the endoprosthesis 300 of FIG. 7 may further include a tapered flange 380 extending axially away from the anchoring portion 320 and radially outward from the linking portion 350 and/or the body portion 340, as seen in FIG. 12. For example, the tapered flange 380 may extend distally from the anchoring portion 320 toward and/or coaxially with the body portion 340. In some embodiments, the tapered flange 380 may at least partially axially overlap the linking portion 350. In at least some embodiments, the polymeric cover 360 may be disposed on the tapered flange 380. In some embodiments, the tapered flange 380 may be embedded within the polymeric cover 360. When the endoprosthesis 300 is placed within the body lumen, the tapered flange 380 may be configured to direct and/or funnel fluid and/or debris from the adjacent and/or branching body lumen into the lumen of the anchoring portion 320. For example, the tapered flange 380 could be deployed within the ampulla of Vater 54 and the tapered flange 380 may be configured to engage with and/or exert a radially outward force against the wall of the body lumen (e.g., the ampulla of Vater 54).

Figure 13:
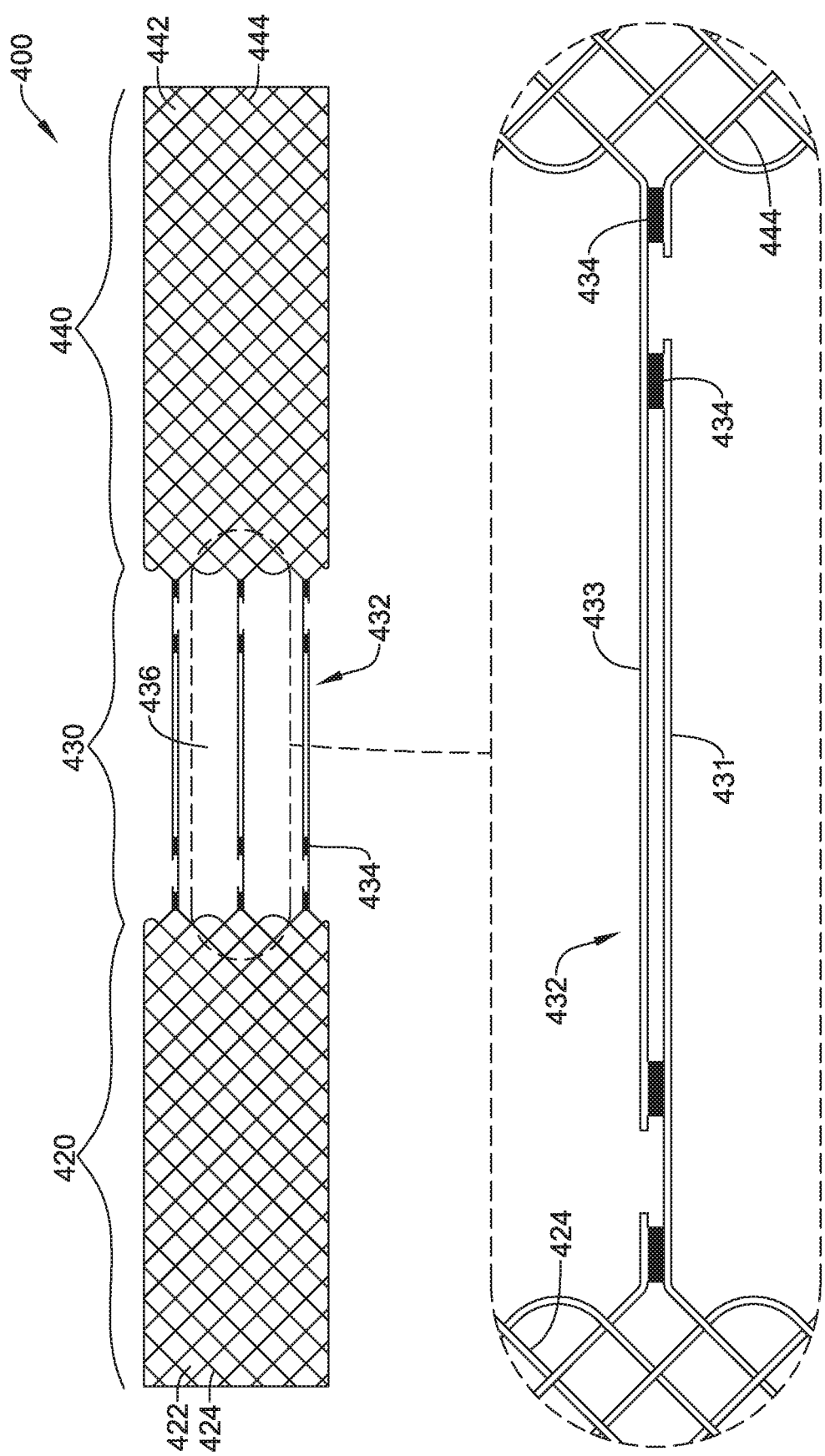
FIG. 13 illustrates aspects of an example endoprosthesis.

FIG. 13 illustrates an example endoprosthesis 400 (which term may be used interchangeably with the term "stent" herein) comprising an expandable framework including a first braided portion 420, a second braided portion 440, and a linking portion 430 extending axially from the first braided portion 420 to the second braided portion 440 along a central longitudinal axis of the endoprosthesis 400 and/or the expandable framework. The endoprosthesis 400 and/or the expandable framework may be configured to shift between a delivery configuration and a deployed configuration. The delivery configuration may be axially elongated and/or radially collapsed or compressed compared to the deployed configuration. The deployed configuration may be axially shortened and/or radially expanded compared to the delivery configuration. In at least some embodiments, the endoprosthesis 400 and/or the expandable framework may be self-expandable. For example, the endoprosthesis 400 and/or the expandable framework may be formed from a shape memory material. In some embodiments, the endoprosthesis 400 and/or the expandable framework may be mechanically expandable. For example, the endoprosthesis 400 and/or the expandable framework may be expandable using an inflatable balloon, using an actuation member, or other suitable means. During delivery to a treatment site, the endoprosthesis 400 and/or the expandable framework may be disposed within a lumen of a delivery sheath in the delivery configuration. Upon removal from the lumen of the delivery sheath, the endoprosthesis 400 and/or the expandable framework may be shifted to the deployed configuration.

As seen in the deployed configuration illustrated in FIG. 13, the first braided portion 420 may have a plurality of first cells 422. The first braided portion 420 may include one or more first filaments 424 interwoven around the central longitudinal axis of the endoprosthesis 400 and/or the expandable framework. The one or more first filaments 424 of the first braided portion 420 may form and/or define the plurality of first cells 422. In some embodiments, the first braided portion 420 may define a lumen extending axially through the first braided portion 420.

The second braided portion 440 may have a plurality of second cells 442. The second braided portion 440 may include one or more second filaments 444 interwoven around the central longitudinal axis of the endoprosthesis 400 and/or the expandable framework. In at least some embodiments, the second braided portion 440 may be coaxial with the first braided portion 420. The one or more second filaments 444 of the second braided portion 440 may form and/or define the plurality of second cells 442. The second braided portion 440 may be substantially tubular and/or may include a lumen extending axially through the second braided portion 440. The second braided portion 440 and/or the one or more second filaments 444 interwoven around the central longitudinal axis of the endoprosthesis 400 and/or the expandable framework may define the lumen extending axially through the second braided portion 440. In at least some embodiments, the lumen extending axially through the second braided portion 440 may be aligned with, may be coaxial with, and/or may intersect with the lumen extending axially through the first braided portion 420 to define a single lumen extending axially through the endoprosthesis 400 and/or the expandable framework.

In some embodiments, the linking portion 430 may include a plurality of longitudinally-oriented struts 432 spacing the first braided portion 420 apart from the second braided portion 440. The plurality of longitudinally-oriented struts 432 may include one or more pairs of a first strut 431 and a second strut 433 extending longitudinally from the first braided portion 420 to the second braided portion 440. The first strut 431 and the second strut 433 may be positioned and/or oriented substantially parallel to each other. In at least some embodiments, the plurality of longitudinally-oriented struts 432, and/or the one or more pairs of the first strut 431 and the second strut 433, may be positioned and/or oriented substantially parallel to the central longitudinal axis of the endoprosthesis 400 and/or the expandable framework.

In at least some embodiments, the linking portion 430 may be formed by manipulating at least a portion of the one or more first filaments 424 of the first braided portion 420 and/or at least a portion of the one or more second filaments 444 of the second braided portion 440. For example, one of the one or more first filaments 424 of the first braided portion 420 may extend away from the first braided portion 420 to form the first strut 431 and one of the one or more second filaments 444 of the second braided portion 440 may extend away from the second braided portion 440 to form the second strut 433. In some embodiments, the first strut 431 and the second strut 433 may be fixedly attached together using one or more welds 434, or other suitable fixation means including but not limited to adhesive bonding, etc., disposed along and between the first strut 431 and the second strut 433 within the linking portion 430.

In some embodiments, at least some of the one or more first filaments 424 of the first braided portion 420 may be "turned back" at a distal end of the first braided portion 420, and at least some of the one or more second filaments 444 of the second braided portion 440 may be "turned back" at a proximal end of the second braided portion 440. In some embodiments, one or more of the "turned back" filaments may be disposed between adjacent pairs of the one or more pairs of the first strut 431 and the second strut 433. In some embodiments, a free end of each of the one or more "turned back" filaments may be fixedly attached (e.g., welded, bonded, etc.) to one or more of the one or more first filaments 424 of the first braided portion 420 proximal of the distal end of the first braided portion 420 and/or within the first braided portion 420, and/or a free end of the one or more "turned back" filaments may be fixedly attached (e.g., welded, bonded, etc.) to one or more of the one or more second filaments 444 of the second braided portion 440 distal of the proximal end of the second braided portion 440 and/or within the second braided portion 440.

In some embodiments, the linking portion 430 define a plurality of longitudinally-extending openings 436 disposed between adjacent struts of the plurality of longitudinally-oriented struts 432. For example, one of the plurality of longitudinally-extending openings 436 may be disposed between A) the second strut 433 of one pair of the one or more pairs of the first strut 431 and the second strut 433 and B) the first strut 431 of an adjacent pair of the one or more pairs of the first strut 431 and the second strut 433. In some embodiments, each longitudinally-extending opening 436 may occupy space equivalent to at least two of the plurality of first cells 422 and/or the plurality of second cells 442. In some embodiments, each longitudinally-extending opening 436 may occupy space equivalent to at least 10 or more, at least 15 or more, at least 20 or more, etc. of the plurality of first cells 422 and/or the plurality of second cells 442. Other configurations are also contemplated.

In some embodiments, the first braided portion 420 and/or the second braided portion 440 may each have an axial length of about 30 millimeters to about 150 millimeters, about 45 millimeters to about 135 millimeters, about 60 millimeters to about 120 millimeters, about 80 millimeters to about 100 millimeters, or another suitable range. In some embodiments, the first braided portion 420 and/or the second braided portion 440 may each have a radial outer dimension or radial extent of about 4 millimeters to about 18 millimeters, about 6 millimeters to about 15 millimeters, about 8 millimeters to about 12 millimeters, or another suitable range. In some embodiments, the linking portion 430 and/or the plurality of longitudinally-oriented struts 432 may have an axial length of about 15 to about 50 millimeters, about 20 to about 35 millimeters, or another suitable range. Other configurations are also contemplated. In at least some embodiments, the linking portion 430 and/or the plurality of longitudinally-oriented struts 432 may be axially shorter than the first braided portion 420 and/or the second braided portion 440. Other configurations are also contemplated.

In some embodiments, the first braided portion 420 and/or the second braided portion 440 may include a flared free end opposite the linking portion 430. In some embodiments, the flared end(s) of the first braided portion 420 and/or the second braided portion 440 opposite the linking portion 430 may have a greater outer diameter and/or outer extent than a remainder of the first braided portion 420, the second braided portion 440, and/or the linking portion 430.

In at least some embodiments, the first braided portion 420 and/or the second braided portion 440 may be braided or woven from the one or more filaments first 424 and/or the one or more second filaments 444, respectively. Other configurations are also contemplated. In some embodiments, the one of the first braided portion 420 and/or the second braided portion 440 may have a denser configuration of filaments and/or smaller cells than the other of the first braided portion 420 and/or the second braided portion 440. In some embodiments, the one or more first filaments 424 of the first braided portion 420 may have a smaller filament diameter or outer extent than the one or more second filaments 444 of the second braided portion 440, and vice versa. In some embodiments, the first braided portion 420 and/or the second braided portion 440 may be separately formed and later joined and/or fixedly attached together, such as by welding, adhesive bonding, mechanical fixation, or other suitable means. Some suitable but non-limiting materials for the endoprosthesis 400, and/or components or elements thereof, for example metallic materials and/or polymeric materials, are described below.

Figure 14:
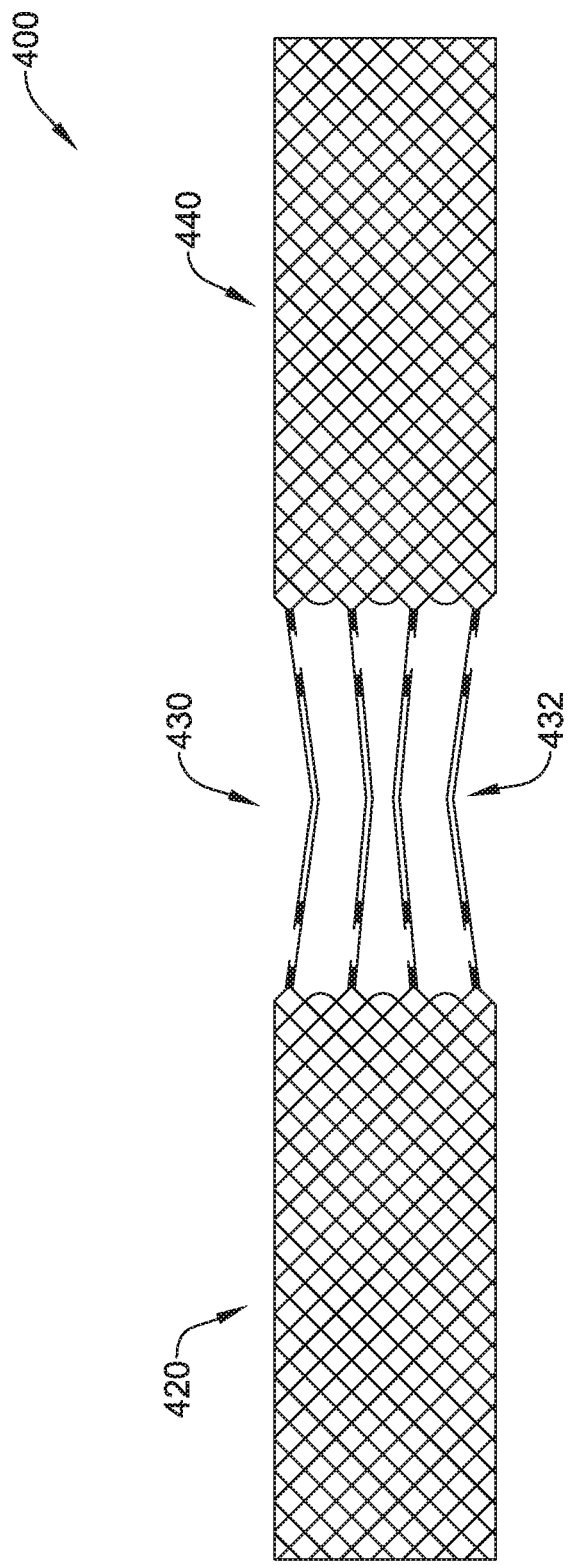
FIG. 14 illustrates an alternative construction of the example endoprosthesis of FIG. 13.

In an alternative configuration, the linking portion 430 of the endoprosthesis 400 and/or the expandable framework may include the plurality of longitudinally-oriented struts 432 being angled radially inward toward the central longitudinal axis of the endoprosthesis 400 and/or the expandable framework between the first braided portion 420 and the second braided portion 440, as seen in FIG. 14. Accordingly, the plurality of longitudinally-oriented struts 432 may be oriented at an oblique angle relative to the central longitudinal axis, the first braided portion 420, and/or the second braided portion 440. Angling the plurality of longitudinally-oriented struts 432 radially inward may reduce and/or prevent interaction of the linking portion 430 and/or the plurality of longitudinally-oriented struts 432 with the wall and/or tissue of the body lumen in which the endoprosthesis 400 is placed, which may reduce irritation of the wall and/or tissue of the body lumen, overgrowth of the plurality of longitudinally-oriented struts 432, and improve removability of the endoprosthesis 400.

Figure 15:
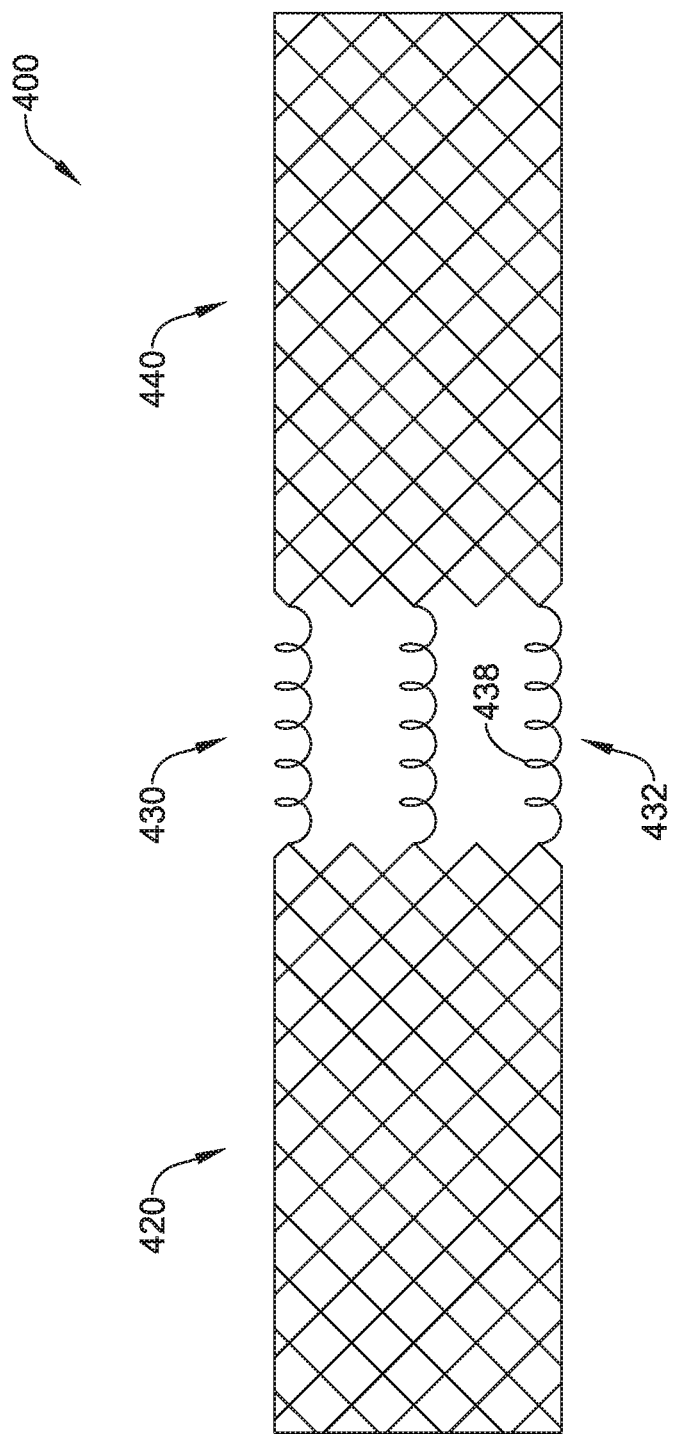
FIG. 15 illustrates an alternative construction of the example endoprosthesis of FIG. 13 in a longitudinally compressed configuration.
Figure 16:
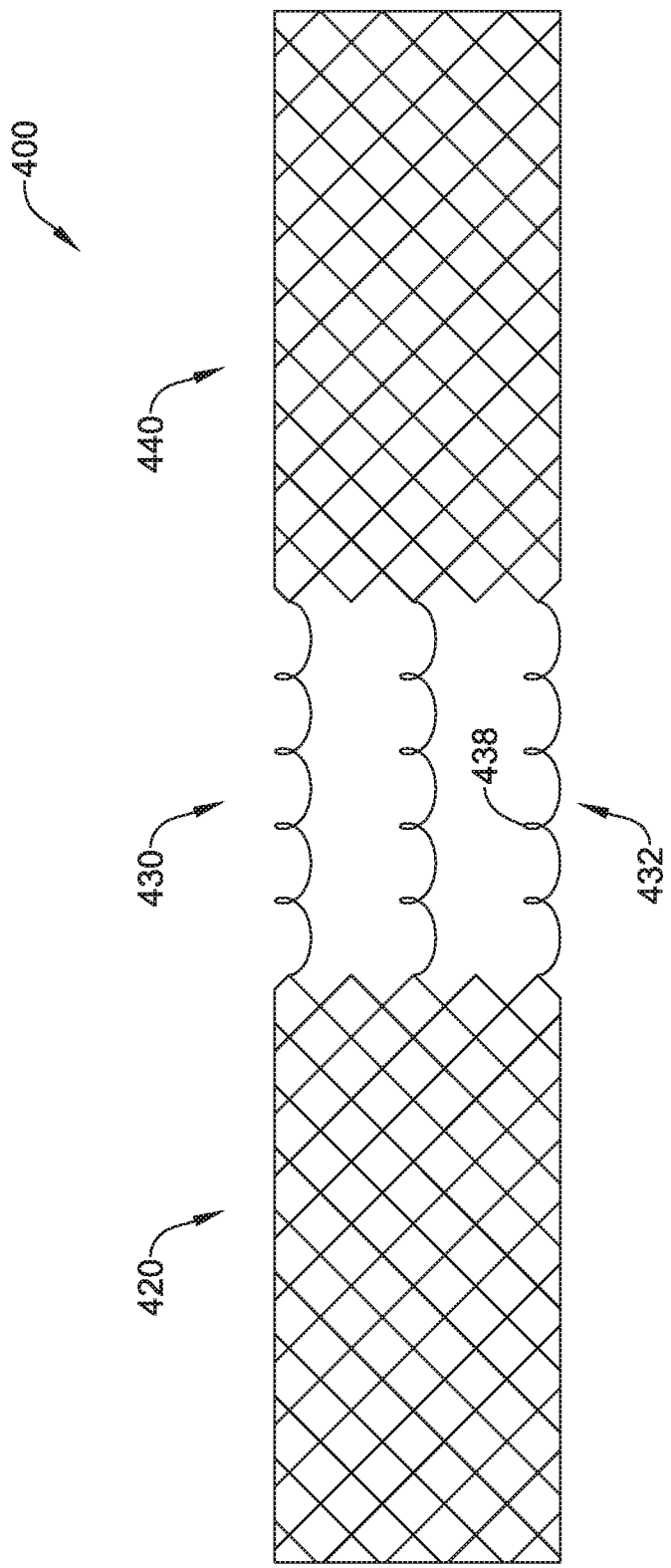
FIG. 16 illustrates the example endoprosthesis of FIG. 15 in a longitudinally extended configuration.

FIGS. 15 and 16 illustrate another alternative configuration of the endoprosthesis 400. In the configuration shown in FIGS. 15 and 16, the linking portion 430 of the endoprosthesis 400 and/or the expandable framework may include the plurality of longitudinally-oriented struts 432, as in the embodiment(s) above. However, each of the plurality of longitudinally-oriented struts 432 of FIGS. 15 and 16 includes a coiled portion 438 extending between the first braided portion 420 and the second braided portion 440. The coiled portion 438 may be spring-like, may include a helical arrangement, and/or may be configured to extend and/or compress axially and/or longitudinally between a longitudinally extended configuration shown in FIG. 15 and a longitudinally compressed configuration shown in FIG. 16. Accordingly, an axial or longitudinal length of the linking portion 430 may be variable to facilitate easier placement of the endoprosthesis 400 within the body lumen. For example, the axial or longitudinal length of the linking portion 430 between the first braided portion 420 and the second braided portion 440 may be adjusted (e.g., shortened or lengthened) to permit placement of the each of the first braided portion 420 and the second braided portion 440 on opposite sides of a junction or bifurcation of two adjoining body lumens.

In at least some embodiments, each of the plurality of longitudinally-oriented struts 432 and/or the coiled portion 438 thereof may be disposed radially within and/or radially inward of an outer extent of the endoprosthesis 400 defined by the first braided portion 420 and/or the second braided portion 440, so as to minimize interaction with the wall and/or tissue of the body lumen in which the endoprosthesis 400 is placed. For example, in some embodiments, the coiled portion 438 may not extend radially outward of the first braided portion 420 or the second braided portion 440. In some embodiments, the coiled portion 438 may not extend radially outward of either one of the first braided portion 420 and the second braided portion 440.

In some embodiments, the first braided portion 420, the linking portion 430, and/or the second braided portion 440 of FIGS. 15 and 16 may be integrally formed as a unitary and/or monolithic structure. In some embodiments, the first braided portion 420, the linking portion 430, and/or the second braided portion 440 may be separately formed and later joined and/or fixedly attached together, such as by welding, adhesive bonding, mechanical fixation, or other suitable means. In some embodiments, the one or more first filaments 424 of the first braided portion 420 may be the one or more second filaments 444 of the second braided portion 440, or vice versa, and the one or more first filaments 424 or the one or more second filaments 444 may also form the plurality of longitudinally-oriented struts 432 and/or the coiled portion 438 thereof. For example, the entire endoprosthesis 400 and/or expandable framework may be formed from the same one or more filaments braided and/or interwoven together continuously as a single monolithic structure.

Figure 17:
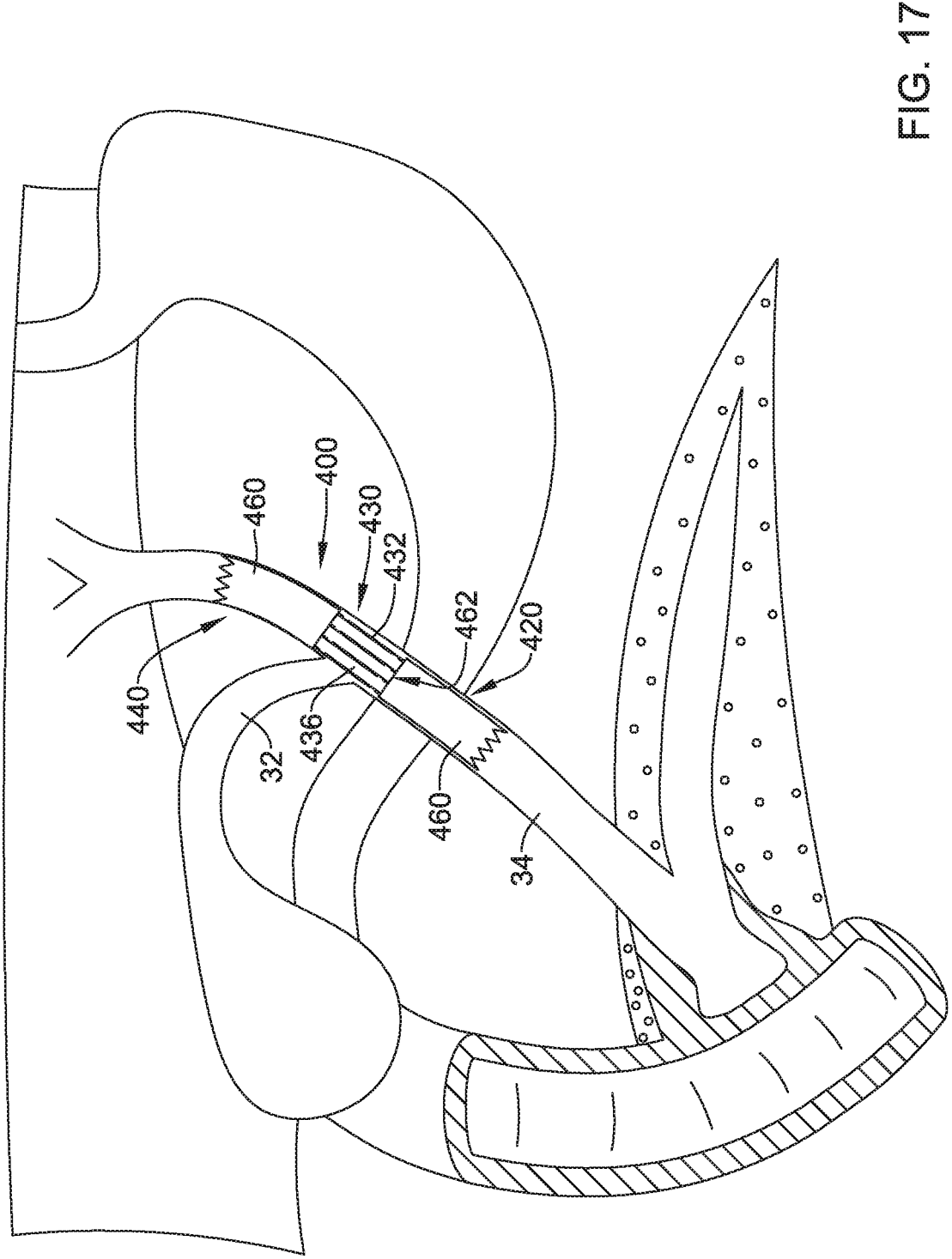
FIG. 17 illustrates an example placement of the endoprosthesis of FIGS. 13-16 in the patient's biliary tree.

As seen in FIG. 17, the endoprosthesis 400 may include a polymeric cover 460 disposed on at least a portion of the expandable framework. In some embodiments, the polymeric cover 460 may be disposed on the first braided portion 420. In some embodiments, the polymeric cover 460 may be disposed on the second braided portion 440. In some embodiments, the polymeric cover 460 may be disposed on both the first braided portion 420 and the second braided portion 440. In some embodiments, the polymeric cover 460 may be disposed on and/or along an outer surface of the expandable framework. In some embodiments, at least a portion of the expandable framework (e.g., the first braided portion 420 and/or the second braided portion 440) may be embedded in the polymeric cover 460. In some embodiments, the polymeric cover 460 may be fixedly or releasably secured to, bonded to, or otherwise attached to expandable framework (e.g., the first braided portion 420 and/or the second braided portion 440).

In some embodiments, the polymeric cover 460 may be impermeable to fluids, debris, medical instruments, etc. The linking portion 430 may be devoid of the polymeric cover 460. As such, the linking portion 430 may be configured to permit passage of fluids, debris, medical instruments, etc. through the side and/or side wall of the endoprosthesis 400 and/or the expandable framework between the plurality of longitudinally-oriented struts 432 and/or through the plurality of longitudinally-extending openings 436. In some embodiments, the linking portion 430 may be at least partially defined by one or more edges 462 of the polymeric cover 460. In some embodiments, the polymeric cover 460 may be coincident with and/or may align with at least a portion of the one or more first filaments 424 of the first braided portion 420 and/or the one or more second filaments 444 of the second braided portion 440. In some embodiments, the one or more edges 462 of the polymeric cover 460 may terminate at the one or more first filaments 424 of the first braided portion 420 and/or the one or more second filaments 444 of the second braided portion 440. In some embodiments, the one or more edges 462 of the polymeric cover 460 may extend between adjacent filaments 424/444. Some suitable but non-limiting materials for the polymeric cover 460 are described below.

FIG. 17 additionally illustrates an example placement of the endoprosthesis 400 within a body lumen (e.g., the common bile duct 34, etc.) being treated. The first braided portion 420, the linking portion 430, and the second braided portion 440 may be disposed within the body lumen (e.g., the common bile duct 34, etc.) being treated. In some embodiments, the body lumen (e.g., the common bile duct 34, etc.) being treated may be partially and/or completely obstructed by a stricture or other blockage. The first braided portion 420 and/or the second braided portion 440 may be configured to dilate at least a portion of the body lumen (e.g., the common bile duct 34, etc.) being treated in the deployed configuration. For example, the first braided portion 420 and/or the second braided portion 440 may be configured to exert a radially outward force upon a wall of the body lumen (e.g., the common bile duct 34, etc.) being treated and/or against a stricture that has formed therein.

In some embodiments, the linking portion 430 may be configured to exert less radially outward force on the wall of the body lumen (e.g., the common bile duct 34, etc.) being treated than the first braided portion 420 and/or the second braided portion 440. For example, in the arrangement shown in FIG. 17, the linking portion 430 may extend across an opening to an adjoining body lumen (e.g., the cystic duct 32, etc.), and may be configured to exert less radially outward force on the opening of the adjoining body lumen (e.g., the cystic duct 32, etc.) than the first braided portion 420 and/or the second braided portion 440 exerts on the body lumen (e.g., the common bile duct 34, etc.) being treated and/or the stricture which has partially obstructed the body lumen (e.g., the common bile duct 34, etc.) being treated.

The endoprosthesis 400 may be positioned using a suitable imaging technique or other means such that the linking portion 430 extends across the opening of an adjoining and/or branching body lumen (e.g., the cystic duct 32, etc.). In the example of FIG. 17, the first braided portion 420 and/or the second braided portion 440 is disposed in the common bile duct 34 and the linking portion 430 extends across the opening of the cystic duct 32. This positioning permits fluid and/or debris within the common bile duct 34 to flow through the lumen of the first braided portion 420 and/or the second braided portion 440 and/or past the stricture without obstructing the cystic duct 32. Other body lumens and/or bifurcations (e.g., junction of the left hepatic duct 12 and the right hepatic duct 14, etc.) and body lumens in other anatomical regions may be treated similarly. Since the orientation of the endoprosthesis 400 is non-directional, placement in a particular orientation is not necessary in order to obtain the benefit(s) of the linking portion 430 extending across the opening of an adjoining and/or branching body lumen, which may reduce procedure time and cost as well as reduce orientation errors that could result in a blocked or partially blocked adjoining and/or branching body lumen. In this way, the linking portion 430 may permit fluid and/or debris from the adjoining body lumen to flow freely into the lumen of the endoprosthesis 400 and through the body lumen that the first braided portion 420 is disposed within.

Figure 18:
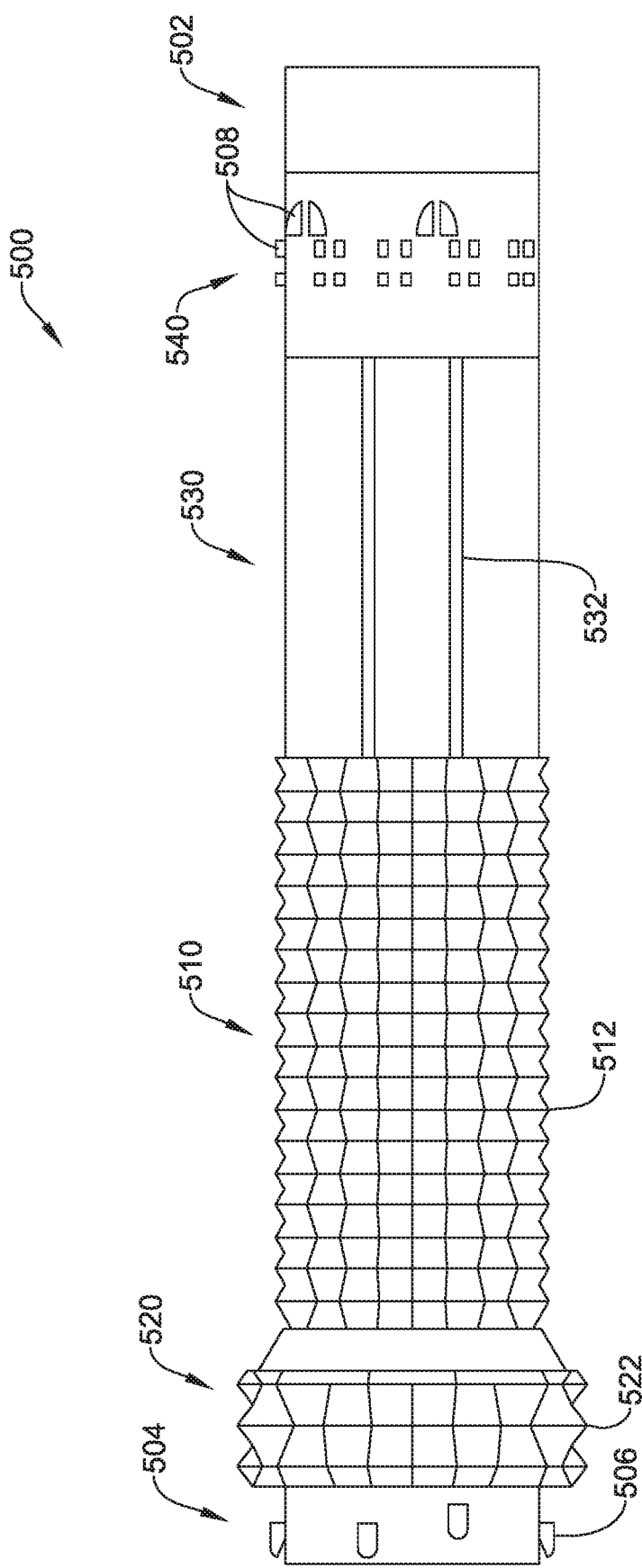
FIG. 18 illustrates an example mandrel usable in a method of manufacturing one or more of the endoprostheses of the disclosure.

FIG. 18 illustrates aspects of an example braiding mandrel 500 for use in manufacturing the endoprosthesis 300 and/or the endoprosthesis 400. The braiding mandrel 500 is a tubular cylindrical member having a distal end 504, a proximal end 502 configured to be secured to a braiding machine, and a longitudinal portion 510 extending between the proximal end 502 and the distal end 504. The braiding mandrel 500 may include a plurality of securement projections 506 disposed proximate the distal end 504 useful for engaging the one or more filaments 344 of the body portion 340 of the endoprosthesis 300 prior to commencement of braiding. In some embodiments, the plurality of securement projections 506 may be formed as raised tabs. In some embodiments, the plurality of securement projections 506 may have a rounded face for ease of securement of the one or more filaments 344 and for safety by generally eliminating shaped and pointed faces on the braiding mandrel 500. In some embodiments, the plurality of securement projections 506 may be useful for bending the one or more filaments 344 about an under portion of the raised tab. In some embodiments, the under portion of the plurality of securement projections 506 may be recessed from the rounded face to secure the one or more filaments 344 thereat. Additionally, in some embodiments, the under portion of the raised tab may be contoured so that the shape of the bend at the end of the body portion 340 of the endoprosthesis 300 opposite the anchoring portion 320 corresponds to the shape of the under portion of the raised tab. In some embodiments, two or more of the one or more filaments 344 may be secured to one and/or each of the plurality of securement projections 506.

The one or more filaments 344 may be braided and/or woven in a one-over and one-under pattern to form the body portion 340 via sinusoidal movement of the carriers of a braiding machine. Other configurations, including but not limited to a two-over and two-under pattern, are also contemplated. The one or more filaments 344 may non-interlockingly engage one another in the braided pattern. Such a non-interlocking braided pattern excludes, if desired, inter-twisting, inter-looping, inter-engaging and the like at intersections and/or crossings of the one or more filaments 344.

The longitudinal portion 510 may include a first plurality of raised projections 512. In some embodiments, the first plurality of raised projections 512 may be arranged in a regular pattern over the longitudinal portion 510 of the braiding mandrel 500 to that adjacent or juxtaposed raised projections 512 form guides or channels therebetween for receiving the one or more filaments 344 during braiding. In at least some embodiments, the first plurality of raised projections 512 may be pyramidally-shaped and/or formed like pyramids having a square or rectangular base and four triangular sides extending radially outward from a central longitudinal axis of the braiding mandrel 500. In some embodiments, the first plurality of raised projections 512 many include truncated and/or rounded top portions. Other shapes and/or configurations are also contemplated. The first plurality of raised projections 512 may be configured and arranged to form guides for receiving the one or more filaments 344 during braiding. In some embodiments, at least a part of the longitudinal portion 510 may be free or partially free of the first plurality of raised projections 512, depending on the characteristics of the endoprosthesis 300 to be produced. For example, the first plurality of raised projections 512 need not necessarily be present along the whole braiding length and/or circumference of the longitudinal portion 510 of the braiding mandrel 500.

The braiding mandrel 500 may optionally include a distal portion 520 proximate the distal end 504, wherein the distal portion 520 has a larger outer extent and/or diameter than the longitudinal portion 510. In some embodiments, the distal portion 520 may be omitted from the braiding mandrel 500. In the absence of the distal portion 520, the longitudinal portion 510 may extend distally to the distal end 504 and/or to a position proximate the distal end 504, wherein the position is disposed just proximal of the plurality of securement projections 506. In some embodiments, there may be a tapered transition between the outer extent and/or diameter of the longitudinal portion 510 and the outer extent and/or diameter of the distal portion 520.

The distal portion 520 may include a second plurality of raised projections 522. In some embodiments, the second plurality of raised projections 522 may be arranged in a regular pattern over the distal portion 520 of the braiding mandrel 500 to that adjacent or juxtaposed raised projections 522 form guides or channels therebetween for receiving the one or more filaments 344 during braiding. In at least some embodiments, the second plurality of raised projections 522 may be pyramidally-shaped and/or formed like pyramids having a square or rectangular base and four triangular sides extending radially outward from the central longitudinal axis of the braiding mandrel 500. In some embodiments, the second plurality of raised projections 522 many include truncated and/or rounded top portions. The second plurality of raised projections 522 may be configured and arranged to form guides for receiving the one or more filaments 344 during braiding. In some embodiments, at least a part of the distal portion 520 may be free or partially free of the first plurality of raised projections 522, depending on the characteristics of the endoprosthesis 300 to be produced. For example, the second plurality of raised projections 522 need not necessarily be present along the whole braiding length and/or circumference of the distal portion 520 of the braiding mandrel 500. The distal portion 520 may be configured to form a flared end of the body portion 340 opposite the anchoring portion 320. In embodiments where the distal portion 520 is omitted, the endoprosthesis 300 may be formed without the flared end. For example, when the distal portion 520 is omitted, the braiding mandrel 500 may have a substantially constant outer extend and/or diameter. Other shapes and/or configurations of the braiding mandrel 500 are also contemplated.

The braiding mandrel 500 may include an intermediate grooved portion 530 disposed between the proximal end 502 and the longitudinal portion 510. In at least some embodiments, the intermediate grooved portion 530 may be disposed immediately adjacent the longitudinal portion 510. The intermediate grooved portion 530 may include a plurality of longitudinally-oriented grooves 532 each configured to receive two filaments of the one or more filaments 344 of the body portion 340 therein to form the first strut 351 and the second strut 353 of the plurality of longitudinally-oriented struts 352 of the linking portion 350. The first strut 351 and the second strut 353 may be welded together at the plurality of welds 354 either while the body portion 340 and the linking portion 350 are disposed on the braiding mandrel 500 (e.g., within the plurality of longitudinally-oriented grooves 532) or after the body portion 340 and the linking portion 350 are removed from the braiding mandrel 500.

Similar to the plurality of securement projections 506 disposed proximate the distal end 504, the braiding mandrel 500 may include a plurality of projections 508 extending radially outward from a proximal portion 540 of the braiding mandrel 500 in some embodiments. In some embodiments, the proximal portion 540 may be optional depending on the specific configuration of endoprosthesis being produced. For example, in some embodiments, the braiding mandrel 500 may include a second longitudinal portion disposed in place of the proximal portion 540 and/or opposite the longitudinal portion 510 relative to the intermediate grooved portion 530 (e.g., the intermediate grooved portion 530 may be disposed between the longitudinal portion 510 and the second longitudinal portion). Such a configuration of the braiding mandrel 500 may be useful for producing the endoprosthesis 400, for example.

A similar braiding mandrel may be used in manufacturing the body portion 140 of the endoprosthesis 100. However, such a mandrel would omit the intermediate grooved portion 530. The body portion 140 of the endoprosthesis 100 would be formed along the longitudinal portion 510 as in the discussion above. The one or more filaments 144 of the body portion 140 may be cut and/or welded to form and/or define the window 150 either while the body portion 140 is disposed on the braiding mandrel 500 or after the body portion 140 has been removed from the braiding mandrel 500. In some embodiments, the anchoring portion 120 may be simultaneously formed on the braiding mandrel 500. In some embodiments, the anchoring portion 120 may be separately formed and subsequently joined to the body portion 140 after the body portion 140 has been removed from the braiding mandrel 500.

A similar braiding mandrel may be used in manufacturing the body portion 240 of the endoprosthesis 200. Again, such a mandrel would omit the intermediate grooved portion 530. The body portion 240 of the endoprosthesis 200 would be formed along the longitudinal portion 510 as in the discussion above. When forming the endoprosthesis 200, a radially-extending projection may be added along the longitudinal portion 510 in place of several of the plurality of raised projections 512. The one or more filaments 244 of the body portion 240 may be braided and/or routed around the radially-extending projection to form the window 250 without cutting and/or welding any of the one or more filaments 244, as is the case with the endoprosthesis 100. In some embodiments, the anchoring portion 220 may be simultaneously formed on the braiding mandrel 500. In some embodiments, the anchoring portion 220 may be separately formed and subsequently joined to the body portion 240 after the body portion 240 has been removed from the braiding mandrel 500.

The materials that can be used for the various components of the endoprosthesis 100/200/300/400 and the various elements thereof disclosed herein may include those commonly associated with medical devices. For simplicity purposes, the following discussion makes reference to the endoprosthesis 100/200/300/400. However, this is not intended to limit the devices and methods described herein, as the discussion may be applied to other elements, members, components, or devices disclosed herein, such as, but not limited to, the expandable framework, the anchoring portion, the body portion, the linking portion, the polymeric cover, and/or elements or components thereof.

In some embodiments, the endoprosthesis 100/200/300/400, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the endoprosthesis 100/200/300/400, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoprosthesis 100/200/300/400 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoprosthesis 100/200/300/400 to achieve the same result.

In some embodiments, a degree of Magnetic Resonance Imaging (MM) compatibility is imparted into the endoprosthesis 100/200/300/400 and/or other elements disclosed herein. For example, the endoprosthesis 100/200/300/400, and/or components or portions thereof, may be made of a material that does not substantially distort the image and create substantial artifacts (i.e., gaps in the image). Certain ferromagnetic materials, for example, may not be suitable because they may create artifacts in an Mill image. The endoprosthesis 100/200/300/400, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the endoprosthesis 100/200/300/400 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the endoprosthesis 100/200/300/400 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the endoprosthesis 100/200/300/400 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An endoprosthesis, comprising:
   an expandable framework including an anchoring portion and a body portion extending axially from the anchoring portion, the body portion having a plurality of body cells defined between adjacent filaments of a plurality of filaments forming the expandable framework, wherein the body portion is braided or woven and the body portion includes the plurality of filaments interwoven around a central longitudinal axis of the expandable framework; and
   a polymeric cover disposed on at least a portion of the expandable framework;
   wherein the anchoring portion includes a first transverse flange disposed at a proximal end of the expandable framework and a second transverse flange disposed proximate the first transverse flange, the second transverse flange located distal of the first transverse flange, the first and the second transverse flanges being configured to secure the anchoring portion at an orifice of a body lumen;
   wherein the body portion extends distally from the second transverse flange toward a distal end of the expandable framework, the body portion including a window through a side of the body portion distal of the second transverse flange, the window occupying space equivalent to at least two of the plurality of body cells;
   wherein a peripheral edge of the window is defined by the plurality of filaments extending around the peripheral edge of the window without cutting any of the plurality of filaments;
   wherein the window is devoid of the polymeric cover and any other structure within a perimeter of the window.

2. The endoprosthesis of claim 1, wherein the first transverse flange and the second transverse flange are axially spaced apart.

3. The endoprosthesis of claim 1, wherein a first body portion opposite the window relative to the central longitudinal axis of the expandable framework is configured to exert less radially outward force on the body lumen than a second body portion opposite the anchoring portion relative to the window.

4. The endoprosthesis of claim 1, wherein a pitch between adjacent ones of the plurality of filaments is variable along a length of the body portion.

5. The endoprosthesis of claim 4, wherein the pitch between the adjacent ones of the plurality of filaments is greatest at opposing axial ends of the window.

6. The endoprosthesis of claim 1, wherein the anchoring portion includes a saddle portion extending axially from the first transverse flange to the second transverse flange.

7. An endoprosthesis, comprising:
   an expandable framework including an anchoring portion at a first end of the expandable framework and a body portion extending axially from the anchoring portion toward a second end of the expandable framework, the body portion having a plurality of body cells defined between adjacent filaments of a plurality of filaments forming the expandable framework; and
   a polymeric cover disposed on at least a portion of the expandable framework;

wherein the anchoring portion includes a first transverse flange and a second transverse flange proximate the first transverse flange, the first transverse flange located closer to the first end of the expandable framework than the second transverse flange, the first and the second transverse flanges being configured to secure the anchoring portion at an orifice of a body lumen;

wherein the body portion extends from the second transverse flange toward the second end of the expandable framework, the body portion including a window through a side of the body portion, the window located closer to the second end of the expandable framework than the second transverse flange, the window occupying space equivalent to at least two of the plurality of body cells;

wherein a peripheral edge of the window is defined by the plurality of filaments extending around the peripheral edge of the window without cutting any of the plurality of filaments;

wherein the window is devoid of the polymeric cover and any other structure within a perimeter of the window.

8. The endoprosthesis of claim 7, wherein the plurality of filaments are braided to form the body portion and the anchoring portion.

9. The endoprosthesis of claim 7, wherein a pitch between the adjacent filaments of the plurality of filaments is variable along a length of the body portion.

10. The endoprosthesis of claim 9, wherein the pitch between the adjacent filaments is greatest at opposing axial ends of the window.

11. The endoprosthesis of claim 7, wherein the anchoring portion includes a saddle portion extending axially from the first transverse flange to the second transverse flange.

12. The endoprosthesis of claim 11, wherein the first transverse flange is configured to be positioned downstream of the orifice of the body lumen, the second transverse flange is configured to be positioned upstream of the orifice of the body lumen, and the saddle portion is configured to extend through the orifice of the body lumen.

13. The endoprosthesis of claim 7, wherein none of the plurality of filaments of the expandable framework extend across the window.

* * * * *